United States Patent
Bruheim et al.

(10) Patent No.: US 9,119,864 B2
(45) Date of Patent: *Sep. 1, 2015

(54) BIOEFFECTIVE KRILL OIL COMPOSITIONS

(71) Applicant: AKER BIOMARINE ANTARCTIC AS, Stamsund (NO)

(72) Inventors: Inge Bruheim, Volda (NO); Snorre Tilseth, Bergen (NO); Daniele Mancinelli, Orsta (NO)

(73) Assignee: AKER BIOMARINE ANTARCTIC AS, Stamsund (NO)

( * ) Notice: Subject to any disclaimer, the term of this patent is extended or adjusted under 35 U.S.C. 154(b) by 0 days.

This patent is subject to a terminal disclaimer.

(21) Appl. No.: 14/620,779

(22) Filed: Feb. 12, 2015

(65) Prior Publication Data
US 2015/0157669 A1 Jun. 11, 2015

Related U.S. Application Data

(63) Continuation of application No. 12/057,775, filed on Mar. 28, 2008.

(60) Provisional application No. 60/920,483, filed on Mar. 28, 2007, provisional application No. 60/975,058, filed on Sep. 25, 2007, provisional application No. 60/983,446, filed on Oct. 29, 2007, provisional application No. 61/024,072, filed on Jan. 28, 2008.

(51) Int. Cl.
| | |
|---|---|
| A61K 35/612 | (2015.01) |
| A61K 9/48 | (2006.01) |
| A61K 31/122 | (2006.01) |
| A61K 31/23 | (2006.01) |
| A61K 31/683 | (2006.01) |
| A61K 31/685 | (2006.01) |
| A61K 45/06 | (2006.01) |
| C11B 3/00 | (2006.01) |
| A61K 31/202 | (2006.01) |
| A61K 31/20 | (2006.01) |
| A61K 31/235 | (2006.01) |

(52) U.S. Cl.
CPC .............. *A61K 35/612* (2013.01); *A61K 9/48* (2013.01); *A61K 9/4858* (2013.01); *A61K 31/122* (2013.01); *A61K 31/20* (2013.01); *A61K 31/202* (2013.01); *A61K 31/23* (2013.01); *A61K 31/235* (2013.01); *A61K 31/683* (2013.01); *A61K 31/685* (2013.01); *A61K 45/06* (2013.01); *C11B 3/006* (2013.01)

(58) Field of Classification Search
CPC .......... A61K 2300/00; A61K 31/122; A61K 31/685; A61K 31/202; A61K 31/683; A61K 35/612; A61K 31/23; A61K 9/4858; A61K 31/232; A61K 35/60; A61K 31/201; A61K 45/06; A61K 31/366; A61K 31/401; A61K 31/505; A61K 36/05; A61K 36/185; A61K 36/324; A61K 36/74; A61K 36/9066; A61K 31/728; A61K 9/04

See application file for complete search history.

(56) References Cited

U.S. PATENT DOCUMENTS

| | | | |
|---|---|---|---|
| 2,652,235 | A | 9/1953 | Samuelsen |
| 4,036,993 | A | 7/1977 | Ikeda |
| 4,119,619 | A | 10/1978 | Rogozhin et al. |
| 4,133,077 | A | 1/1979 | Jasniewicz |
| 4,251,557 | A | 2/1981 | Shimose et al. |
| 4,505,936 | A | 3/1985 | Meyers et al. |
| 4,714,571 | A | 12/1987 | Kearns et al. |
| 4,749,522 | A | 6/1988 | Kamarei |
| 4,814,111 | A | 3/1989 | Kearns et al. |
| 5,006,281 | A | 4/1991 | Rubin et al. |
| 5,266,564 | A | 11/1993 | Modolell |
| 5,434,183 | A | 7/1995 | Larsson-Backstrom |
| 6,214,396 | B1 | 4/2001 | Barrier |
| 6,346,276 | B1 | 2/2002 | Tanouchi et al. |
| 6,537,787 | B1 | 3/2003 | Breton |
| 6,800,299 | B1 | 10/2004 | Beaudoin et al. |
| 7,488,503 | B1 | 2/2009 | Porzio et al. |
| 7,666,447 | B2 | 2/2010 | Rockway |
| 8,030,348 | B2 | 10/2011 | Sampalis |

(Continued)

FOREIGN PATENT DOCUMENTS

| | | |
|---|---|---|
| AU | 2002322233 | 2/2003 |
| BR | 8701265 | 3/1987 |

(Continued)

OTHER PUBLICATIONS

EP Opposition filed Feb. 13, 2014 by Olympic Seafood AS, EP Patent Application No. EP08718910I6.

(Continued)

*Primary Examiner* — Debbie K Ware
(74) *Attorney, Agent, or Firm* — Casimir Jones, S.C.

(57) ABSTRACT

This invention discloses new krill oil compositions characterized by having high amounts of phospholipids, astaxanthin esters and/or omega-3 contents. The krill oils are obtained from krill meal using supercritical fluid extraction in a two stage process. Stage 1 removes the neutral lipid by extracting with neat supercritical $CO_2$ or $CO_2$ plus approximately 5% of a co-solvent. Stage 2 extracts the actual krill oils by using supercritical $CO_2$ in combination with approximately 20% ethanol. The krill oil materials obtained are compared with commercially available krill oil and found to be more bioeffective in a number of areas such as anti-inflammation, anti-oxidant effects, improving insulin resistances and improving blood lipid profile.

19 Claims, 19 Drawing Sheets

(56) References Cited

U.S. PATENT DOCUMENTS

| | | | |
|---|---|---|---|
| 8,057,825 B2* | 11/2011 | Sampalis | 424/522 |
| 8,278,351 B2 | 10/2012 | Sampalis | |
| 8,383,675 B2 | 2/2013 | Sampalis | |
| 8,697,138 B2 | 4/2014 | Bruheim et al. | |
| 2002/0076468 A1 | 6/2002 | Saxby | |
| 2003/0044495 A1 | 3/2003 | Kagan et al. | |
| 2003/0113432 A1 | 6/2003 | Yoshitomi et al. | 426/643 |
| 2004/0241249 A1 | 12/2004 | Sampalis | |
| 2006/0078625 A1 | 4/2006 | Rockway | |
| 2006/0193962 A1 | 8/2006 | Kamiya et al. | 426/615 |
| 2008/0166419 A1 | 7/2008 | Sones | |
| 2008/0166420 A1 | 7/2008 | Sones | |
| 2010/0143571 A1 | 6/2010 | Breivik | |
| 2010/0160659 A1 | 6/2010 | Catchpole | |
| 2011/0130458 A1 | 6/2011 | Breivik | |

FOREIGN PATENT DOCUMENTS

| | | | |
|---|---|---|---|
| CA | 1098900 | | 4/1981 |
| CA | 2251265 | | 4/2000 |
| CL | 40348 | | 7/1997 |
| EP | 0609078 | | 8/1994 |
| EP | 670306 | | 6/1995 |
| EP | 1127497 | | 8/2001 |
| EP | 1392623 | | 3/2004 |
| EP | 1406641 | | 4/2004 |
| EP | 1542670 | | 6/2005 |
| EP | 0973532 | | 9/2005 |
| EP | 1660071 | | 5/2006 |
| EP | 1689413 | | 8/2006 |
| EP | 1743531 | | 1/2007 |
| EP | 1631280 | | 3/2008 |
| EP | 1123368 | | 4/2008 |
| EP | 1406641 | | 1/2009 |
| EP | 1419768 | | 1/2009 |
| EP | 1292294 | | 3/2009 |
| EP | 1706106 | | 7/2009 |
| EP | 1385500 | | 7/2010 |
| GB | 2097014 | | 10/1982 |
| GB | 921537 | | 6/1999 |
| JP | A-S51-125774 | | 11/1976 |
| JP | A-S52-114046 | | 9/1977 |
| JP | 60-153779 | | 8/1985 |
| JP | 61281159 | | 12/1986 |
| JP | 02049091 | | 2/1990 |
| JP | 2215351 | | 8/1990 |
| JP | 4012665 | | 1/1992 |
| JP | 2963152 | | 2/1992 |
| JP | 04057853 | | 2/1992 |
| JP | 3081692 | | 7/1994 |
| JP | 2524217 | | 8/1996 |
| JP | H08-231391 | | 9/1996 |
| JP | 3344887 | | 7/1997 |
| JP | 3611222 | | 8/1997 |
| JP | 2001-158736 | A | 6/2001 |
| JP | 2003-003192 | A | 1/2003 |
| JP | 2003-048831 | A | 2/2003 |
| JP | 2003-146883 | A | 5/2003 |
| JP | 3467794 | | 9/2003 |
| JP | 2003-530448 | | 10/2003 |
| JP | 2003-531857 | A | 10/2003 |
| JP | 3486778 | | 10/2003 |
| JP | 2004-525180 | A | 8/2004 |
| JP | 2004-534800 | | 11/2004 |
| JP | 2004-536059 | A | 12/2004 |
| JP | 3678317 | | 5/2005 |
| JP | 2005-245379 | A | 9/2005 |
| JP | 2006-502196 | A | 1/2006 |
| JP | 2006-069948 | A | 3/2006 |
| JP | 2006-083136 | A | 3/2006 |
| JP | 2006-290784 | A | 10/2006 |
| JP | 2006-316073 | A | 11/2006 |
| JP | 2006-328014 | A | 12/2006 |
| JP | 2006-528233 | A | 12/2006 |
| JP | 2007-502805 | A | 2/2007 |
| JP | 2007-509131 | A | 4/2007 |
| JP | 2007-126455 | A | 5/2007 |
| JP | 2007-518764 | A | 7/2007 |
| JP | 2007-246404 | A | 9/2007 |
| SU | 220741 | | 1/1971 |
| WO | 86/06082 | | 10/1986 |
| WO | 89/01031 | | 2/1989 |
| WO | 89/10960 | | 11/1989 |
| WO | 90/05765 | | 5/1990 |
| WO | 93/24142 | | 12/1993 |
| WO | 97/38585 | | 10/1997 |
| WO | 97/39759 | | 10/1997 |
| WO | 98/34498 | | 8/1998 |
| WO | 99/39589 | | 8/1999 |
| WO | 00/23546 | | 4/2000 |
| WO | 00/25608 | | 5/2000 |
| WO | 00/38708 | | 7/2000 |
| WO | 01/28526 | | 4/2001 |
| WO | 01/82928 | | 11/2001 |
| WO | 02/083122 | | 10/2002 |
| WO | 02/092540 | | 11/2002 |
| WO | 02/102394 | | 12/2002 |
| WO | 03/011873 | | 2/2003 |
| WO | 03/013497 | | 2/2003 |
| WO | 2004/028529 | | 4/2004 |
| WO | 2004/047554 | | 6/2004 |
| WO | 2004/100943 | | 11/2004 |
| WO | 2004/112767 | | 12/2004 |
| WO | 2005/004393 | | 1/2005 |
| WO | 2005/018632 | | 3/2005 |
| WO | 2005/037848 | | 4/2005 |
| WO | 2005/038037 | | 4/2005 |
| WO | 2005/070411 | | 8/2005 |
| WO | 2006/030552 | | 3/2006 |
| WO | 2006/111633 | | 10/2006 |
| WO | 2007/080514 | | 7/2007 |
| WO | 2007/080515 | | 7/2007 |
| WO | 2007/108702 | | 9/2007 |
| WO | 2007/123424 | | 11/2007 |
| WO | 2008/006607 | | 1/2008 |
| WO | 2008/072563 | | 6/2008 |
| WO | 2008/117062 | | 10/2008 |
| WO | 2009/027692 | | 3/2009 |

OTHER PUBLICATIONS

Brzustowicz, Michael R., et al., "Controlling Membrane Cholesterol Content. A Role for Polyunsaturated (Docosahexaenoate) Phospholipids," Biochemistry (2002), 41, pp. 12509-12519.

Jong-Ho Lee, "A Review: Antioxygenic and Peroxide-decomposing Activities of Antarctic Krill Lipids," J. Korean Soc. Food Mutr. 13(3) pp. 326-333 (1984).

Ki Woong Cho, et al., "Lipid and Fatty Acid Composition of the Antarctic Krill *Euphausia superba*," Ocean Research 21(2): 109-116 (1999).

Hvattum, Erlend, et al., "Effect of soybean oil and fish oil on individual molecular species of Atlantic salmon . . . ", Journal of Chromatography B, 748 (2000) 137-149.

Igarashi, Daisuke, et al., "Positional Distribution of DHA and EPA in Phosphatidylcholine and Phosphatidylethanolamine from Different Tissues of Squids," J. Oleo Sci. vol. 50, No. 9 (2001).

Tochizawa, Kaoru, et al., "Effects of Phospholipds Containing Docosahexaenoic Acid on Differentiation and Growth of HL-60 Human Promyelocytic Leukemia Cells," J. Jpn. Oil Chem. Soc. vol. 46, No. 4 (1997).

Zerouga, Mustapha, et al., "Comparison of phosphatidylcholines containing one or two docosahexaenoic acyl chains on properties of phospholipid monolayers and bilayers," Biochimica et Biophysica Acta 1236 (1995) 266-272.

Eung-Ho Lee, et al., "Studies on the Processing of Krill Sauce," J. Korean Soc. Food Nutr. 13(1) 97-106 (1984).

Hyun-Ku Kim, et al., "Effects of Cooking and Drying Methods on the Polar Lipds Composition of Shrimp," Korean J. Food Sci. Technol. vol. 21, No. 1, pp. 25-30 (1989).

Shon, Mi-Yae, et al., "Effects of Krill and Cadmium on Lipid Composition of Plasma in Cholesterol-Fed Rats," J. Korean Soc. Food Nutr. 23(1), 38-43 (1994).

Summons Materials downloaded from ESPACE on Dec. 16, 2014 for EP Patent Application No. 08 718 910.6.

(56) References Cited

OTHER PUBLICATIONS

Valeri, D., et al., "Visocities of Fatty acids, triglycerides and their binary mixtures," JAOCS 74 (1997) pp. 1221-1226.
CRC 2013-2014, 94th ed., pp. 6-231-6-235.
"Neptune Technologies & Bioressources Soon to Obtain a Major Patent in Over 30 Countries" ("2001 Press Release,").
Action Closing Prosecution, '348 patent.
Apr. 2, 2012 Response to Office Action, '351 patent.
Balassa et al., Microencapsulation in the Food Industry, Critical Reviews in Food Technology, 2:2, 245-265 (1971) ("Balassa").
Bell and Dick, Molecular Species Composition of the Major Diacyl Glycerophospholipids from Muscle, Liver, Retina and Brain of Cod (*Gadus morhua*), Lipids, vol. 26, No. 8, pp. 565-573 (1991) ("Bell and Dick").
Bell, Molecular Species Analysis of Phosphoglycerides from the Ripe Roes of Cod, Lipids, vol. 24, No. 7 (1989).
Bell, Molecular Species Composition of Phosphatidylcholine from Crypthecodinium cohnii in Relation to Growth Temperature Lipids 25, 115-118 (1990).
Bergelson (ed.), Lipid Biochemical Preparations, Chapter I.1, pp. 1-13 (1980) ("Bergelson").
Bottino, N.R., "Lipid Composition of Two Species of Antarctic Krill: *Euphausia superba* and *E. crystallorophias*," Comp. Biochem. Physiol., 1975, vol. 50B, pp. 479-484 ("Bottino").
Buchi R-220 Rotovapor® Manual.
Buda, Structural order of membranes and composition of phospholipids in fish brain cells during thermal acclimatization, Proc. Natl. Acad. Sci. USA vol. 91, pp. 8234-8238, Aug. 1994.
Certificate of translation of Ex. 1072: Fisheries Agency, General Report on Research and Development of Techniques in Processing and Utilization of Marine Products, Chapter 6, Development of technology for recovery of valuable substances (astaxanthin) from krill, by Takao Fujita, pp. 273-307 (Mar. 1985); Japanese language document.
Certificate of translation of Ex. 1074: Japanese Patent No. 60-153779, entitled "Nutritional Supplement".
Certificate of translation of Ex. 1076: Japanese Patent Publication No. H08-231391, entitled "Medicine for Improvement of Dementia Symptoms".
Certification of translation of Ex. 1070: Japanese Unexamined Patent Application Publication No. 02-215351.
Certified translation of Ex. 1070: Japanese Unexamined Patent Application Publication No. 02-215351, titled Krill Phospholipids Fractioning Method ("Maruyama,"); Certificate of Translation provided as Ex. 1071.
Certified translation of Ex. 1072: Fisheries Agency, General Report on Research and Development of Techniques in Processing and Utilization of Marine Products, Chapter 6, Development of technology for recovery of valuable substances (astaxanthin) from krill, by Takao Fujita, pp. 273-307 (Mar. 1985) ("Fujita") ; Certificate of Translation provided as Ex. 1073.
Certified translation of Ex. 1074: Japanese Patent No. 60-153779, entitled "Nutritional Supplement" ("Fukuoka"); Certificate of Translation provided as Ex. 1075.
Certified translation of Ex. 1076: Japanese Patent Publication No. H08-231391, entitled "Medicine for Improvement of Dementia Symptoms" ("Yasawa"); Certificate of Translation provided as Ex. 1077.
Declaration of Bjorn Ole Haugsgjerd in support of Inter Partes Review of U.S. Pat. No. 8,278,351 ("Haugsgjerd").
Declaration of Bjorn Ole Haugsgjerd submitted during inter partes reexamination of parent patent U.S. Pat. No. 8,030,348 ("Haugsgjerd '348 Decl.").
Declaration of Dr. Albert Lee in Support of Inter Partes Review of U.S. Pat. No. 8,278,351 ("Lee").
Declaration of Dr. Albert Lee in Support of Inter Partes Review of U.S. Pat. No. 8,383,675 ("Lee").
Declaration of Dr. Chong Lee submitted during inter partes reexamination of parent patent U.S. Pat. No. 8,030,348 ("Yeboah Reexam Decl.").
Declaration of Dr. Earl White submitted during prosecution of parent patent U.S. Pat. No. 8,030,348 ("2011 White Decl.").
Declaration of Dr. Ivar Storrø in support of Inter Partes Review of U.S. Pat. No. 8,278,351 ("Storrø").
Declaration of Dr. Ivar Storrø in support of Inter Partes Review of U.S. Pat. No. 8,383,675 ("Storrø").
Declaration of Dr. Jacek Jaczynski from inter partes reexamination of the parent patent U.S. Pat. No. 8,030,348 ("Jaczynski Reexam. Decl.").
Declaration of Dr. Jaczynski submitted during prosecution of parent patent U.S. Pat. No. 8,278,351 (Jaczynski '351 Decl.).
Declaration of Dr. Jeff Moore in Support of Inter Partes Review of U.S. Pat. No. 8,278,351 ("Moore").
Declaration of Dr. Jeff Moore in Support of Inter Partes Review of U.S. Pat. No. 8,383,675 ("Moore").
Declaration of Dr. Richard van Breemen in Support of Inter Partes Review of U.S. Pat. No. 8,278,351 ("Van Breemen").
Declaration of Dr. Richard van Breemen in Support of Inter Partes Review of U.S. Pat. No. 8,383,675 ("Van Breemen").
Declaration of Dr. Shahidi submitted during inter partes reexamination of parent patent U.S. Pat. No. 8,030,348 (Shahidi Reexam. Decl.).
Declaration of Dr. Shahidi submitted during prosecution of parent patent U.S. Pat. No. 8,278,351 (Shahidi '351 Decl.).
Declaration of Dr. Suzanne Budge in Support of Inter Partes Review of U.S. Pat. No. 8,278,351 ("Budge").
Declaration of Dr. Suzanne Budge in Support of Inter Partes Review of U.S. Pat. No. 8,383,675 ("Budge").
Declaration of Dr. Thomas Brenna in support of Inter Partes Review of U.S. Pat. No. 8,278,351.
Declaration of Dr. Thomas Brenna in support of Inter Partes Review of U.S. Pat. No. 8,383,675.
Declaration of Dr. Thomas Gundersen submitted during inter partes reexamination of parent patent U.S. Pat. No. 8,030,348 ("Gundersen Decl.").
Declaration of Dr. Tina Sampalis submitted during inter partes reexamination of parent patent U.S. Pat. No. 8,030,348 (Sampalis).
Declaration of Dr. Van Breemen submitted during Ex parte Reexamination of the '351 patent (Van Breemen '351 Reexam. Decl.
Declaration of Dr. Van Breemen submitted during Inter partes Reexamination of the '348 patent (Van Breemen '348 Reexam Decl.
Declaration of Dr. Yeboah submitted during inter partes reexamination of parent patent U.S. Pat. No. 8,030,348 ("Yeboah Reexam Decl.").
Declaration of Dr. Yeboah submitted during prosecution of parent patent U.S. Pat. No. 8,278,351 ("Yeboah '351 Decl.").
Eichberg, "Lecithin—It Manufacture and Use in the Fat and Oil Industry," Oils and Soap 51-54, 1939 ("Eichberg").
Expert Witness Report of Dr. Theodore Welch submitted in relation to ITC Investigation No. 337-TA-877 ("Welch").
Farkas, Composition and Physical State of Phospholipids in Calanoid Copepods from India and Norway, LIPIDS, vol. 23, No. 6 (1988).
Final Prospectus dated May 11, 2001 ("Final Prospectus").
Fisheries Agency, General Report on Research and Development of Techniques in Processing and Utilization of Marine Products, Chapter 6, Development of technology for recovery of valuable substances (astaxanthin) from krill, by Takao Fujita, pp. 273-307 (Mar. 1985); Japanese language document.
Folch, et al., A Simple Method for the Isolation and Purification of Total Lipids from Animal Tissues. J. Biol. Chem., 226, 497-509 (1957).
Grant of Request for Ex parte Reexamination of the '351 patent.
Grit et al., Hydrolysis of phosphatidylcholine in aqueous liposome dispersions, Int. J. Pharmaceutics 50:1-6 (1989).
Henderson et al., Lipid Composition of the Pineal Organ from Rainbow Trout (*Oncorhynchus mykiss*), Lipids, vol. 29, No. 5, pp. 311-317 (1994) ("Henderson").
Herman and Groves, The Influence of Free Fatty Acid Formation on the pH of Phospholipid-Stabilized Triglyceride Emulsions, Pharmaceutical Research 10(5):774-776 (1993).

(56) References Cited

OTHER PUBLICATIONS

Itano Refrigerated Food Co., Ltd., Bio & High Technology Announcement and Natural Astaxanthin & Krill Lecithin, pp. 1-16 (on or before Dec. 28, 1994) ("Itano").
Johnson and Lucas, Comparison of Alternative Solvents for Oils Extraction, JAOCS 60(2):229-242 (1983).
Le Grandois et al., Investigation of Natural Phosphatidylholine Sources: Separation and Identification by Liquid Chromatography—Electrospray Ionization—Tandem Mass Spectrometry (LC-ESI-MS2) of Molecular Species, J. Agric. Food Chem., 57, 6014-20 (2009) ("Le Grandois").
Lin et al., Effect of Dietary N-3 Fatty Acids Upon the PhospholipidMolecular Species of the Monkey Retina, Invest Ophthalmol Vis Sci. 1994;35:794-803.
Medina et al., C Nuclear Magnetic Resonance Monitoring of Free Fatty Acid Release After Fish Thermal Processing, J. Amer. Oil Chem. Soc. 71(5):479-82 (1994).
Oct. 24, 2012 Office Action, '675 patent.
Office Action dated Jan. 5, 2012, '351 patent.
U.S. Appl. No. 60/307,842 (Priority document for the '351 patent).
Supplemental Declaration of Bjorn Ole Haugsgjerd submitted during inter partes reexamination of parent patent U.S. Pat. No. 8,030,348 ("Haugsgjerd '348 Supp. Decl.").
Supplemental Declaration of Dr. Earl White submitted during inter partes reexamination of parent patent U.S. Pat. No. 8,030,348 ("White Supp. Reexam. Decl").
Supplemental Declaration of Dr. Earl White submitted during prosecution of parent patent U.S. Pat. No. 8,278,351 ("White Supp. Decl").
Supplemental Declaration of Dr. Thomas Gundersen submitted during inter partes reexamination of parent patent U.S. Pat. No. 8,030,348 ("Gundersen Supp. Decl.").
Suzuki, T. and Shibata, N., "The utilization of Antarctic krill for human food," Food Rev. Int'l, 6:1, 119-147 (1990) ("Suzuki").
Takahashi et al., Compositional Changes in Molecular Species of Fish Muscle Phosphatidylcholine During Storage, Bull. Fac. Fish. Hokkaido Univ. 37(1), 80-84 1986.
Takahashi et al., Molecular Species of Fish Muscle Lecithin, Bulletin of the Japanese Society of Scientific Fisheries 48(12), 1803-1814 (1982).
Takahashi et al., Prediction of Relative Retention Value of the Individual Molecular Species of Diacyl Glycerolipid on High Performance Liquid Chromatography, Bull. Fac. Fish. Hokkaido Univ. 38(4), 398-404. 1987.
Tanaka, Biosynthesis of 1,2-dieicosapentaenoyl-sn-glycero-3-phosphocholine in Caenorhabditis elegans, Eur. J. Biochem. 263, 189±194 (1999).
Tocher, Chapter 6, Glycerophospholipid metabolism, Biochemistry and molecular biology of fishes, vol. 4, Hochachka and Mommsen (eds.)(1995).
Watanabe et al., Effective Components in Cuttlefish Meal and Raw Krill for Improvement of Quality of Red Seabream Pagrus major Eggs, Nippon Suisan Gakkaishi 57(4):681-694 (1991)("Watanabe").
WHO News and Activities, Bulletin of the World Health Organization, 73(4), pp. 547-551 (1995) ("WHO Bulletin").
European Search Report, EP Patent Application No. EP12187516, mailed Jun. 10, 2013.
CN Office Action mailed Apr. 27, 2012, JP Patent Application No. 200880112125.6 (and English translation).
Fricke, et al., Lipid, Sterol and Fatty Acid Composition of Antarctic Krill (*Euphausia superba* Dana), Lipids (1984) 19(11): 821-827.
Fricke, et al., 1-O-Alkylglycerolipids in Antarctic Krill (*Euphausia superba* Dana), Comp. Biochem. Physiol. (1986) 85B(1): 131-134.
Gordeev, K.Y., et al. "Fatty Acid Composition of the Main Phospholipids of the Antarctic Krill, *Euphausia superba*," Chem. Nat. Cmpds. (1990) 26(2), pp. 143-147.
Grantham (1977) Southern Ocean Fisheries Survey Programme, FAO Rome, GLO/SO/77/3: 1-61.
Raventos et al., Application and Posssibilities of Supercritical CO2 Extraction in Food Processing Industry: An Overview, Food Science and Technology International (2002) 8: 269-284.
Tanaka, T., et al., Platelet-activating Factor (PAF)-like Phospholoipds Formed during Peroxidation of Phosphatidylcholines from Different Foodstuffs, Biosci. Biotech. Biochem. (1995) 59 (8), pp. 1389-1393.
Winther, et al., Elucidation of Phosphatidylcholine Composition in Krill Oil Extracted from *Euphausia superba*, Lipids (2011) 46: 25-36.
JP Office Action mailed Feb. 23, 2012, JP Patent Application No. 2010-522444 (and English translation).
Dec. 8, 2011 Office Action, KR Patent Application No. 10-2010-7006897 and its English translation.
Sikorski, E., "The Utilization of Krill for Food," Food Process Eng., 1:845-855 (1980).
Budzinskli, E., et al., "Possibilities of processing and marketing of products made from Antarctic Krill", FAO Fish. Tech. Pap. (268) 46 pages (1985).
Bunea R., et al.., "Evaluation of the Effects of Neptune Krill Oil on the Clinical Course of Hyperlipidemia," Alternative Medicine Review, Thorne Research Inc., Sandpoint, US, vol. 9, No. 4, Jan. 1, 2004.
Gordeev, K.Y., et al. "Fatty Acid Composition of the Main Phospholipids of the Antarctic Krill, *Euphausia superba*," Khim. Prirod. Soed. 2 (1990), pp. 181-187.
Ando and Hatano, 1988, "Isolation of apolipoproteins from carotenoid-carrying lipoprotein in the serum of chum salmon, Oncorhynchus keta", J. Lipid Research, 29: 1264-1271.
Aoi et al., 2003, "Astaxanthin limits exercise-induced skeletal and cardiac muscle damage in mice", Antioxidants & Redox Signaling, 5(1): 139-44.
Britton, 1985, "General Carotenoid Methods", Methods in Enzymology, vol. 111, pp. 113-149.
Calder, 2006, "n-3 polyunsaturated fatty acids, inflammation, and inflammatory diseases", Am. J. Clin. Nutr., 83: 1505S.
Charest et al., 2001, "Astaxanthin Extraction from Crawfish Shells by Supercritical CO2 with Ethanol as Cosolvent", J. Aquatic Food Product Technology, 10(3): 79-93.
Chen and Meyers, 1982, "Extraction of Astaxanthin Pigment from Crawfish Waste Using a Soy Oil Process", J. Food Sci., 47: 892-896.
Clarke, 1980, "The Biochemical Composition of Krill, *Euphausia superba* dana, from South Georgia", J. Exp. Mar. Biol. Ecol., 43: 221-236.
Czeczuga, 1974, "Comparative Studies of Carotenoids in the Fauna of the Gullmar Fjord (Bohuslan, Sweden). II. Crustacea: Eupagurus bernhardus, Hyas coarctatus and Upogebia deltaura", Marine Biology, 28: 95-98.
De Ritter and Purcell, 1981, "Carotenoid Analytical Methods", Carotenoids as Colorants and Vitamin A Precursors: Technological and Nutritional Applications, pp. 815-882.
Deutch, 1995, "Menstrual pain in Danish women correlated with low n-3 polyunsaturated fatty acid intake", Eur. J. Clin. Nutr., 49(7): 508-16.
Diez et al., 2003, "The role of the novel adipocyte-derived hormone adiponectin in human disease", Eur. J. Endocrinol., 148(3): 293-300.
Ellingsen et al., 1987, "Biochemistry of the autolytic processes in Antarctic krill post mortem. Autoproteolysis." Biochem. J. 246, 295-305.
Emodi, 1978, "Carotenoids: Properties and Applications", Food Technology, 32(5): 38.
Felix-Valenzuela et al., 2001, "Supercritical CO2/Ethanol Extraction of Astaxanthin from Blue Crab (*Callinectes sapidus*) Shell Waste", Journal of Food Process Engineering, 24: 101-112.
Fox and Scheer, 1941, "Comparative Studies of the Pigments of Some Pacific Coast Echinoderms", The Biological Bulletin, 441-455.
Fricke, et al., 1984, "Lipid, Sterol and Fatty Acid Composition of Antarctic Krill (*Euphausia superba* Dana)", Lipids, 19(11): 821-827.

(56) References Cited

OTHER PUBLICATIONS

Geusens et al., 1994, "Long-term effect of omega-3 fatty acid supplementation in active rheumatoid arthritis. A 12-month, double-blind, controlled study", Arthritis Rheum., 37(6): 824-9.
Gilchrist and Green, 1960, "The Pigments of Artemia", Proceedings of the Royal Society, Series B Biological Sciences, vol. 152 No. 946, pp. 118-136.
Goodwin and Srisukh, 1949, "Some Observations on Astaxanthin Distribution in Marine Crustacea", Department of Biochemistry, University of Liverpool, pp. 268-270.
Gulyaev and Bugrova, 1976 Removing fats from the protein paste "Okean". Konservnaya I Ovoshchesushil'naya Promyshlennost, (4), 37-8.
Hardardottir and Kinsella, 1988, "Extraction of Lipid and Cholesterol from Fish Muscle with Supercritical Fluids" Journal of Food Science, 53(6): 1656-1658.
International Aqua Feed, 2006, vol. 9.
International Search Report and Written Opinion for PCT/GB2008/002934, Dated Mar. 11, 2009.
International Search Report and Written Opinion for PCT/IB2010/000512; dated Jun. 24, 2010.
International Search Report for PCT/IB2007/000098, dated: Jun. 26, 2007.
Itoh et al., 2007; "Increased adiponectin secretion by highly purified eicosapentaenoic acid in rodent models of obesity and human obese subjects", Arteriosclerosis, Thrombosis, and Vascular Biology; 27(9): 1918-1925.
Johnson et al., 1978, "Simple Method for the Isolation of Astaxanthin from the Basidiomycetous Yeast Phaffia rhodozyma", Applied and Environmental Microbiology, 35(6): 1155-1159.
Kolakowska, 1989, "Krill lipids after frozen storage of about one year in relation to storage time before freezing", Die Nahrung Food, 33(3): 241-244.
Kris-Etherton et al., 2002, "Fish Consumption, Fish Oil, Omega-3 Fatty Acids, and Cardiovascular Disease", Circulation, 106:2747-2757.
Kristensen et al., 1989, "Dietary supplementation with n-3 polyunsaturated fatty acids and human platelet function: a review with particular emphasis on implications for cardiovascular disease", J. Intern. Med. Suppl. 731:141-50.
Kunesova et al., 2006, "The influence of n-3 polyunsaturated fatty acids and very low calorie diet during a short-term weight reducing regimen on weight loss and serum fatty acid composition in severely obese women", Physiol Res.; 55(1):63-72.
Laight et al., 1999, "F2-isoprostane evidence of oxidant stress in the insulin resistant, obese Zucker rat: effects of vitamin E", Eur. J. Pharmacol. 377(1): 89-92.
Lambertson and Braekkan, 1971, "Method of Analysis of Astaxanthin and its Occurrence in some Marine Products," J. Sci. Food. Agr., vol. 22(2): 99-101.
Libby et al., 2006, "Inflammation and Atherothrombosis: From Population Biology and Bench Research to Clinical Practice", J. Amer. Coll. Card., 48 (9, Suppl. A): A33-A46.
Lopez et al., 2004, "Selective extraction of astaxanthin from crustaceans by use of supercritical carbon dioxide", Talanta, 64: 726-731.
Mandeville, 1991, "Isolation and Identification of Carotenoid Pigments, Lipids and Flavor Active Components from Raw Commercial Shrimp Waste", Food Biotechnology, 5(2): 185-195.
Meyers and Bligh, 1981, "Characterization of Astaxanthin Pigments from Heat-Processed Crawfish Waste", J. Agric. Food Chem., 29: 505-508.
Meyers, 1977, "Using Crustacean Meals and Carotenoid-Fortified Diets", Feedstuffs, vol. 49(19).
Meyers, 1994, "Developments in world aquaculture, feed formulations, and role of carotenoids", Pure & Appl. Chem, vol. 66(5): 1069-1076.
Mills et al., 1989, "Dietary N-6 and N-3 fatty acids and salt-induced hypertension in the borderline hypertensive rat", Lipids, 24(1): 17-24.
Moates and Van Bentem, 1990, "Separating out the value", Food Science and Technology Today, 4(4): 213-214.
Nikolaeva, 1967 "Amino acid composition of protein-coagulate in krill", VNIRO, 63:161-4.
Phleger, et al. (2002) "Interannual and between species comparison in the lipids, fatty acids, and sterols of Antarctic krill from the US AMLR Elephant Island survey area: 1997 and 1998". Comp Biochem Physiol 131B:733-747.
Popp-Snijders et al., 1987, "Dietary supplementation of omega-3 polyunsaturated fatty acids improves insulin sensitivity in non-insulin-dependent diabetes", Diabetes Res. 4(3): 141-7.
Sachindra, 2006, "Recovery of carotenoids from shrimp waste in organic solvents", Waste Management, 26: 1092-1098.
Saether et al., 1986, "Lipids of North Atlantic krill", J Lipid Res., 27(3):274-85.
Shahidi et al., 1998, "Carotenoid Pigments in Seafoods and Aquaculture" Critical Reviews in Food Science, 38(1): 1-67.
Sidehu et al., 1970, "Biochmical Composition and Nutritive Value of Krill (*Euphausia superb* dana)", J. Sci Food Agr., vol. 21, 293-296.
Simopoulos, 1991, "Omega-3 fatty acids in health and disease and in growth and development", Am. Clin. Nutr. 54:438-63.
Somiya, 1982, "'Yellow lens' eyes of a stomiatoid deep-sea fish, Malacosteus niger", Proc. R. Soc. Lond., 215: 481-489.
Takaichi et al., 2003, "Fatty Acids of astaxanthin esters in krill determined by mild mass spectrometry", Comparative Biochemistry and Physiology Part B, Biochemistry and Molecular Biology, Elsevier, Oxford, vol. 136, Jan. 1, 2003, p. 317-322.
Tanaka et al., 2004, "Extraction of Phospholipids from Salmon Roe with Supercritical Carbon Dioxide and an Entrainer", J. Oleo Sci, 53(9): 417-424.
Tanaka et al., 2005, "Extraction of Phospholipids from Unused Natrual Resources with Supercritical Carbon Dioxide and an Entrainer", Journal of Oleo Science, vol. 54(11): 569-576.
Todoric et al., 2006, "Adipose tissue inflammation induced by high-fat diet in obese diabetic mice is prevented by n-3 polyunsaturated fatty acids", Diabetologia, 49(9): 2109-2119.
Tou et al., 2007, "Krill for human consumption: nutritional value and potential health benefits.", Nutrition Rev 65(2):63-77.
Trayhurn et al., 2004, "Adipokines: inflammation and the pleiotropic role of white adipose tissue", Br. J. Nutrition, 92(3): 347-355.
Trebble et al., 2003, "Inhibition of tumour necrosis factor-alpha and interleukin 6 production by mononuclear cells following dietary fish-oil supplementation in healthy men and response to antioxidant co-supplementation", Br. J. Nutrition, 90(2): 405-412.
Ukkola et al., 2002, "Adiponectin: a link between excess adiposity and associated comorbidities?", J. Mol. Med., 80(11): 696-702.
Van Der Veen et al., 1971 "The Lipids of Krill (*Euphausia* Species) and Red Crab (*Pleuroncodes planipes*)", Lipids, 6(7): 481-485.
Virtue, et al. 1996, Reproductive trade-off in male Antarctic krill, *Euphausia superba*, Marine Biology, vol. 126, No. 3, pp. 521-527.
Yamaguchi et al., 1983, "The Composition of Carotenoid Pigments in the Antarctic Krill *Euphausia superba*", Bulletin of the Japanese Society of Scientific Fisheries, 49(9): 1411-1415.
Yamaguchi et al., 1986, "Supercritical Carbon Dioxide Extraction of Oils From Antarctic Krill," Journal of Agricultural and Food Chemistry, vol. 34, pp. 904-907.
Yanase M; 1974, "Modification of a Russian method for separation of heat-coagulated protein from Antarctic krill", Database FSTA (online); International Food Information Service (IFIS); Frankfurt-Main, DE.
Yen et al., 1994, "Effect of dietary omega-3 and omega-6 fatty acid sources on PUVA-induced cutaneous toxicity and tumorogenesis in the hairless mouse", Arch. Dermatol. Res., 286(6): 331-6.
Database WPI Week 200682, Thomson Scientific, London, GB, 2006.
English Abstract; JP 2003-531857; See abstract from corresponding WO 2001/082928 filed herewith.
English Abstract; JP 2004-525180; See abstract from corresponding WO 2002/083122 filed herewith.
English Abstract; JP 2006-528233; See abstract from corresponding WO 2004/100943 filed herewith.

(56) References Cited

OTHER PUBLICATIONS

English Abstract; JP 2007-502805; See abstract from corresponding WO 2005/018632 filed herewith.
English Abstract; JP 2007-509131; See abstract from corresponding WO 2005/037848 filed herewith.
English Abstract; JP 2007-518764; See abstract from corresponding WO 2005/070411 filed herewith.
English Abstract; JP 2004-536059; See abstract from corresponding WO 2002/09254 filed herewith.
English Abstract; JP 2006-502196; See abstract from corresponding WO 2004/028529 filed herewith.

* cited by examiner

BIOEFFECTIVE KRILL OIL COMPOSITIONS

CROSS-REFERENCE TO RELATED APPLICATIONS

This application is a continuation of pending U.S. patent application Ser. No. 12/057,775, filed Mar. 28, 2008, which claims the benefit of U.S. Provisional Patent Application No. 60/920,483, filed Mar. 28, 2007, U.S. Provisional Patent Application No. 60/975,058, filed Sep. 25, 2007, U.S. Provisional Patent Application No. 60/983,446, filed Oct. 29, 2007, and U.S. Provisional Patent Application No. 61/024,072, filed Jan. 28, 2008, all of which are incorporated by reference herein in their entirety.

FIELD OF THE INVENTION

This invention relates to extracts from Antarctic krill that comprise bioactive fatty acids.

BACKGROUND OF THE INVENTION

In the Southern Ocean, off the coast of Antarctica, Antarctic krill (*Euphausia superba*) can be found in large quantities, ranging from 300-500 million metric tons of biomass. It feeds on phytoplankton during the short Antarctic summer. During winter, however, its food supply is limited to ice algae, bacteria, marine detritus as well as depleting body protein for energy.

In order to isolate the krill oil from the krill, solvent extraction methods have been used. See, e.g., WO 00/23546. Krill lipids have been extracted by placing the material in a ketone solvent (e.g. acetone) in order to extract the lipid soluble fraction. This method involves separating the liquid and solid contents and recovering a lipid rich fraction from the liquid fraction by evaporation. Further processing steps include extracting and recovering by evaporation the remaining soluble lipid fraction from the solid contents by using a solvent such as ethanol. See, e.g., WO 00/23546. The compositions produced by these methods are characterized by containing at least 75 µg/g astaxanthin, preferably 90 µg/g astaxanthin. Another krill lipid extract disclosed contained at least 250 µg/g canastaxanthin, preferably 270 µg/g canastaxanthin.

Krill oil compositions have been described as being effective for decreasing cholesterol, inhibiting platelet adhesion, inhibiting artery plaque formation, preventing hypertension, controlling arthritis symptoms, preventing skin cancer, enhancing transdermal transport, reducing the symptoms of premenstrual symptoms or controlling blood glucose levels in a patient. See, e.g., WO 02/102394. In yet another application, a krill oil composition has been disclosed comprising a phospholipid and/or a flavonoid. The phospholipid content in the krill lipid extract could be as high as 60% w/w and the EPA/DHA content as high as 35% (w/w). See, e.g., WO 03/011873.

Furthermore, nutraceuticals, pharmaceuticals and cosmetics comprising the phospholipid extract were disclosed. Previously, it was also shown that supercritical fluid extraction using neat $CO_2$ could be used to prevent the extraction of phospholipids in order to extract the neutral lipid fraction from krill, which comprised of esterified and free astaxanthin. See, e.g., Yamaguchi et al., *J. Agric. Food Chem.* (1986), 34(5), 904-7. Supercritical fluid extraction with solvent modifier has previously been used to extract marine phospholipids from salmon roe, but has not been previously used to extract phospholipids from krill meal. See, e.g., Tanaka et al., *J. Oleo Sci.* (2004), 53(9), 417-424.

The methods described above rely on the processing of frozen krill that are transported from the Southern Ocean to the processing site. This transportation is both expensive and can result in degradation of the krill starting material. Data in the literature showing a rapid decomposition of the oil in krill explains why some krill oil currently offered as an omega-3 supplement in the marketplace contains very high amounts of partly decomposed phosphatidylcholine and also partly decomposed glycerides. Saether et al., Comp. Biochem Phys. B 83B(1): 51-55 (1986). The products offered also contain high levels of free fatty acids.

What is needed in the art are methods for processing krill that do not require transport of frozen krill material over long distances and the products produced by those methods.

SUMMARY OF THE INVENTION

In a first aspect of the invention is a composition characterized by comprising at least 65% (w/w) phospholipids.

In another aspect of the invention is a composition obtained from aquatic or marine sources, characterized by comprising 65% (w/w) phospholipids.

In yet another aspect of the invention is a composition obtained from krill, characterized by comprising at least 65% (w/w) phospholipids.

In another aspect of the invention is a composition obtained from krill, characterized by comprising at least 65% (w/w) phospholipids and at least 39% omega-3 fatty acids (w/w).

In yet another aspect of the invention is a composition obtained from krill, characterized by comprising at least 65% (w/w) phospholipids, at least 39% omega-3 fatty acids (w/w) and at least 580 mg/kg astaxanthin esters.

In another aspect of the invention is a composition obtained from krill, characterized by comprising at least 39% omega-3 fatty acids (w/w) and at least 580 mg/kg astaxanthin esters.

In yet another aspect of the invention is a composition obtained from krill, characterized by comprising at least 65% (w/w) phospholipids and at least 580 mg/kg astaxanthin esters.

In yet another aspect, the present invention provides a krill oil effective for reducing insulin resistance, improving blood lipid profile, reducing inflammation or reducing oxidative stress.

In some embodiments, the present invention provides compositions comprising: from about 3% to 10% ether phospholipids on a w/w basis; from about 35% to 50% non-ether phospholipids on w/w basis, so that the total amount of ether phospholipids and non-ether phospholipids in the composition is from about 48% to 60% on a w/w basis; from about 20% to 45% triglycerides on a w/w basis; and from about 400 to about 2500 mg/kg astaxanthin. In some embodiments, the ether phospholipids are selected from the group consisting of alkylacylphosphatidylcholine, lyso-alkylacylphosphatidylcholine, alkylacylphosphatidylethanolamine, and combinations thereof. In some embodiments, the ether lipids are greater than 90% alkylacylphosphatidylcholine. In some embodiments, the non-ether phospholipids are selected from the group consisting of phosphatidylcholine, phosphatidylserine, phosphatidylethanolamine and combinations thereof. In some embodiments, krill oil composition comprises a blend of lipid fractions obtained from krill. In some preferred embodiments, krill is *Euphausia superba*, although other krill species also find use in the present invention. Other krill species include, but are not limited to *E. pacifica, E. frigida, E. longirostris, E. triacantha, E. vallentini, Meganyc-*

*tiphanes norvegica, Thysanoessa raschii* and *Thysanoessa inermis*. In some embodiments, the compositions comprise from about 25% to 30% omega-3 fatty acids as a percentage of total fatty acids and wherein from about 80% to 90% of said omega-3 fatty acids are attached to said phospholipids. In some embodiments, the present invention provides a capsule containing the foregoing compositions.

In further embodiments, the present inventions provide compositions comprising: from about 3% to 10% ether phospholipids on a w/w basis; and from about 400 to about 2500 mg/kg astaxanthin. In some embodiments, the compositions further comprise from about 35% to 50% non-ether phospholipids on w/w basis, so that the total amount of ether phospholipids and non-ether phospholipids in the composition is from about 38% to 60% on a w/w basis. In some embodiments, the compositions further comprise from about 20% to 45% triglycerides on a w/w basis. In some embodiments, the ether phospholipids are selected from the group consisting of alkylacylphosphatidylcholine, lyso-alkylacylphosphatidylcholine, alkylacylphosphatidylethanolamine, and combinations thereof. In some embodiments, the ether lipids are greater than 90% alkylacylphosphatidylcholine. In some embodiments, the non-ether phospholipids are selected from the group consisting of phosphatidylcholine, phosphatidylserine, phosphatidylethanolamine and combinations thereof. In some embodiments, krill oil composition comprises a blend of lipid fractions obtained from krill. In some preferred embodiments, krill is *Euphausia superba*, although other krill species also find use in the present invention. Other krill species include, but are not limited to *E. pacifica, E. frigida, E. longirostris, E. triacantha, E. vallentini, Meganyctiphanes norvegica, Thysanoessa raschii* and *Thysanoessa inermis*. In some embodiments, the compositions comprise about 25% to 30% omega-3 fatty acids as a percentage of total fatty acids and wherein from about 80% to 90% of said omega-3 fatty acids are attached to said phospholipids. In some embodiments, the present invention provides a capsule containing the foregoing compositions.

In some embodiments, the present invention provides a composition comprising at least 65% (w/w) of phospholipids, said phospholipids characterized in containing at least 35% omega-3 fatty acid residues. In some preferred embodiments, the composition is derived from a marine or aquatic biomass. In some further preferred embodiments, the composition is derived from krill. In some embodiments, the composition comprises less than 2% free fatty acids. In some embodiments, composition comprises less than 10% triglycerides. In some preferred embodiments, the phospholipids comprise greater than 50% phosphatidylcholine. In some embodiments, the composition comprises at least 500 mg/kg astaxanthin esters. In some embodiments, the composition comprises at least 500 mg/kg astaxanthin esters and at least 36% (w/w) omega-3 fatty acids. In some embodiments, the composition comprises less than about 0.5 g/100 g total cholesterol. In some embodiments, the composition comprises less than about 0.45% arachidonic acid (w/w).

In some embodiments, the present invention provides a krill lipid extract comprising at least 500, 100, 1500, 2000, 2100, or 2200 mg/kg astaxanthin esters and at least 36% (w/w) omega-3 fatty acids. In further embodiments, the present invention provides a krill lipid extract comprising at least 100 mg/kg astaxanthin esters, at least 20% (w/w) omega-3 fatty acids, and less than about 0.45% arachidonic acid (w/w).

In some embodiments, the present invention provides methods comprising administering the foregoing compositions to a subject in an amount effective for reducing insulin resistance, reducing inflammation, improving blood lipid profile and reducing oxidative stress.

In some embodiments, the present invention provides a krill lipid extract comprising greater than about 80% triglycerides and greater than about 90, 100, 500, 1000, 1500, 200, 2100 or 2200 mg/kg astaxanthin esters. In some embodiments, the krill lipid extract is characterized in containing from about 5% to about 15% omega-3 fatty acid residues. In some embodiments, the krill lipid extract is characterized in containing less than about 5% phospholipids. In some embodiments, the krill lipid extract is characterized in comprising from about 5% to about 10% cholesterol.

In some embodiments, the present invention provides a krill meal composition comprising less than about 50 g/kg total fat. In some embodiments, the krill meal composition comprises from about 5 to about 20 mg/kg astaxanthin esters. In some embodiments, the krill meal composition comprises greater than about 65% protein. In some embodiments, the krill meal composition of comprises greater than about 70% protein. In some further embodiments, the present invention provides an animal feed comprising the krill meal composition.

In some embodiments, the present invention provides methods of increasing flesh coloration in an aquatic species comprising feeding said aquatic species a composition comprising the krill meal described above. In some embodiments, the present invention provides methods of increasing growth and overall survival rate of aquatic species by feeding the krill meal described above.

In some embodiments, the present invention provides methods of producing krill oil comprising: a) providing krill meal; and b) extracting oil from said krill meal. In some embodiments, the krill meal is produced by heat-treating krill. In some embodiments, the krill meal is stored prior to the extraction step. In some embodiments, the extracting step comprises extraction by supercritical fluid extraction. In some embodiments, the supercritical fluid extraction is a two step process comprising a first extraction step with carbon dioxide and a low concentration of a co-solvent (e.g., from about 1-10% co-solvent) and a second extraction step with carbon dioxide and a high concentration of a co-solvent (e.g., from about 10-30% co-solvent). In preferred embodiments, the co-solvent is a $C_1$-$C_3$ monohydric alcohol, preferably ethanol. In some embodiments, the present invention provides oil produced by the foregoing method.

In some embodiments, the present invention provides methods of production of krill oil comprising: a) providing fresh krill; b) treating said fresh krill to denature lipases and phospholipases in said fresh krill to provide a denatured krill product; and c) extracting oil from said denatured krill product. In some embodiments, the denaturation step comprises heating of said fresh krill. In some embodiments, the denaturation step comprises heating said fresh krill after grinding. In some embodiments, the methods further comprise storing said denatured krill product at room temperature or below between the denaturation step and the extraction step. In some embodiments, the enzyme denaturation step is achieved by application of heat. In some embodiments, the extraction step comprises use of supercritical carbon dioxide, with or without use of a polar modifier. In some embodiments, the extraction step comprises use of ethanol. In some embodiments, the extraction step is comprises ethanol extraction followed by acetone to precipitation of phospholipids. In some embodiments, the denatured krill product is a meal. In some embodiments, the present invention provides oil produced by the foregoing method.

In some embodiments, the present invention provides a composition comprising oil extracted from krill having a phosphatidylcholine content of greater then about 50% (w/w). In some embodiments, the oil has a phosphatidylcholine content of greater then about 70% (w/w). In some embodiments, the oil has a phosphatidylcholine content of greater then about 80% (w/w). In some embodiments, the composition comprises less than 2% free fatty acids. In some embodiments, the composition comprises less than 10% triglycerides. In some embodiments, the composition comprises at least 500 mg/kg astaxanthin esters. In some embodiments, the composition comprises less than about 0.45% arachidonic acid (w/w).

In some embodiments, the present invention provides composition comprising odorless krill oil. In some embodiments, the odorless krill oil comprises less than about 10 mg/kg (w/w) trimethylamine. In some further embodiments, the present invention provides an odorless krill oil produced by the method comprising: extracting a neutral krill oil from a krill oil containing material by supercritical fluid extraction to provide a deodorized krill material, wherein said neutral krill oil contains odor causing compounds and extracting a polar krill oil from said deodorized krill material by supercritical fluid extraction with a polar entrainer to provide an essentially odorless krill oil.

In some embodiments, the present invention provides a composition comprising krill oil containing less than about 70 micrograms/kilogram (w/w) astaxanthin esters. In some embodiments, the compositions comprise less than about 50 micrograms/kilogram (w/w) astaxanthin esters. In some embodiments, the compositions comprise less than about 20 micrograms/kilogram (w/w) astaxanthin esters. In some embodiments, the compositions comprise less than about 5 micrograms/kilogram (w/w) astaxanthin esters.

In some embodiments, the present invention provides a krill oil produced by the process comprising: pumping fresh krill from a trawl onto a ship, heating the krill to provide a krill material, and extracting oil from the krill material.

In further embodiments, the present invention provides a blended krill oil composition comprising: from about 45% to 55% w/w phospholipids; from about 20% to 45% w/w triglycerides; and from about 400 to about 2500 mg/kg astaxanthin. In some embodiments, the blended krill oil product comprises a blend of lipid fractions obtained from *Euphausia superba*. In some embodiments, the composition comprises from about 25% to 30% omega-3 fatty acids as a percentage of total fatty acids and wherein from about 80% to 90% of said omega-3 fatty acids are attached to said phospholipids.

In still other embodiments, the present invention provides a *Euphausia superba* krill oil composition comprising: from about 30% to 60% w/w phospholipids; from about 20% to 50% triglycerides; from about 400 to about 2500 mg/kg astaxanthin; and from about 20% to 35% omega-3 fatty acids as a percentage of total fatty acids in said composition, wherein from about 70% to 95% of said omega-3 fatty acids are attached to said phospholipids.

In still further embodiments, the present invention provides a dietary supplement comprising encapsulated *Euphausia superba* krill oil comprising from about 30% to 60% w/w phospholipids; from about 20% to 50% triglycerides; from about 400 to about 2500 mg/kg astaxanthin; and from about 20% to 35% omega-3 fatty acids as a percentage of total fatty acids in said composition, wherein from about 70% to 95% of said omega-3 fatty acids are attached to said phospholipids.

In some embodiments, the present invention provides methods of making a *Euphausia superba* krill oil composition comprising: contacting *Euphausia superba* with a polar solvent to provide a polar extract comprising phospholipids; contacting *Euphausia superba* with a neutral solvent to provide a neutral extract comprising triglycerides and astaxanthin; combining said polar extract and said neutral extract to provide *Euphausia superba* krill oil comprising from about 30% to 60% w/w phospholipids; from about 20% to 50% triglycerides; from about 400 to about 2500 mg/kg astaxanthin; and from about 20% to 35% omega-3 fatty acids as a percentage of total fatty acids in said composition, wherein from about 70% to 95% of said omega-3 fatty acids are attached to said phospholipids. In some embodiments, the methods further comprise the step of encapsulating the *Euphausia superba* krill oil. In some embodiments, the present invention provides a *Euphausia superba* krill oil produced by the methods described above.

In some embodiments, the present invention provides methods of producing a dietary supplement comprising: contacting *Euphausia superba* with a polar solvent to provide an polar extract comprising phospholipids; contacting *Euphausia superba* with a neutral solvent to provide a neutral extract comprising triglycerides and astaxanthin; combining said polar extract and said neutral extract to provide *Euphausia superba* krill oil comprising from about 30% to 60% w/w phospholipids; from about 20% to 50% triglycerides; from about 400 to about 2500 mg/kg astaxanthin; and from about 20% to 35% omega-3 fatty acids as a percentage of total fatty acids in said composition, wherein from about 70% to 95% of said omega-3 fatty acids are attached to said phospholipids; and encapsulating said *Euphausia superba* krill oil.

In some embodiments, the present invention provides methods of reducing diet-induced hyperinsulinemia, insulin insensitivity, muscle mass hypertrophy, serum adiponectin reduction or hepatic steatosis comprising in a subject exposed to a high fat diet: administering to said subject exposed to a high fat diet an effective amount of a krill oil composition under conditions such that a condition selected from the group consisting of diet-induced hyperinsulinemia, insulin insensitivity, muscle mass hypertrophy, serum adiponectin reduction and hepatic steatosis is reduced. The present invention is not limited to any particular krill oil composition. In some embodiments, the krill oil composition is a *Euphausia superba* krill oil composition. The present invention is not limited to any particular formulation of krill oil. In some embodiments, the krill oil composition is encapsulated. In some preferred embodiments, the effective amount of a krill oil composition is from 0.2 grams to 10 grams of said krill oil composition. In some embodiments, the krill oil composition comprises: from about 45% to 55% w/w phospholipids; from about 20% to 45% w/w triglycerides; and from about 400 to about 2500 mg/kg astaxanthin. In some embodiments, the krill oil composition comprises a blend of lipid fractions obtained from *Euphausia superba*. In some embodiments, the krill oil composition comprises from about 25% to 30% omega-3 fatty acids as a percentage of total fatty acids and wherein from about 80% to 90% of said omega-3 fatty acids are attached to said phospholipids. In some embodiments, the krill oil composition comprises from about 30% to 60% w/w phospholipids; from about 20% to 50% triglycerides; from about 400 to about 2500 mg/kg astaxanthin; and from about 20% to 35% omega-3 fatty acids as a percentage of total fatty acids in said composition, and wherein from about 70% to 95% of said omega-3 fatty acids are attached to said phospholipids.

In some embodiments, the present invention provides methods of reducing diet-induced hyperinsulinemia, insulin insensitivity, muscle mass hypertrophy, serum adiponectin reduction or hepatic steatosis comprising in a subject consuming a high fat diet or a normal fat diet: administering to said subject consuming a high fat diet or a normal fat diet an effective amount of a krill oil composition under conditions such that a condition selected from the group consisting of diet-induced hyperinsulinemia, insulin insensitivity, muscle mass hypertrophy, serum adiponectin reduction and hepatic steatosis is reduced. The present invention is not limited to any particular krill oil composition. In some embodiments, the krill oil composition is a *Euphausia superba* krill oil composition. The present invention is not limited to any particular formulation of krill oil. In some embodiments, the krill oil composition is encapsulated. In some preferred embodiments, the effective amount of a krill oil composition is from 0.2 grams to 10 grams of said krill oil composition. In some embodiments, the krill oil composition comprises: from about 45% to 55% w/w phospholipids; from about 20% to 45% w/w triglycerides; and from about 400 to about 2500 mg/kg astaxanthin. In some embodiments, the krill oil composition comprises a blend of lipid fractions obtained from *Euphausia superba*. In some embodiments, the krill oil composition comprises from about 25% to 30% omega-3 fatty acids as a percentage of total fatty acids and wherein from about 80% to 90% of said omega-3 fatty acids are attached to said phospholipids. In some embodiments, the krill oil composition comprises from about 30% to 60% w/w phospholipids; from about 20% to 50% triglycerides; from about 400 to about 2500 mg/kg astaxanthin; and from about 20% to 35% omega-3 fatty acids as a percentage of total fatty acids in said composition, and wherein from about 70% to 95% of said omega-3 fatty acids are attached to said phospholipids.

In some embodiments, the present invention provides methods of inducing diuresis in a subject comprising: administering to said subject an effective amount of a krill oil composition under conditions such that diuresis is induced. In some embodiments, the present invention provides methods of increasing muscle mass in a subject, comprising: administering to said subject an effective amount of a krill oil composition under conditions such that muscle mass is increased. In some embodiments, the present invention provides methods of decreasing protein catabolism in a subject, comprising: administering to said subject an effective amount of a krill oil composition under conditions such that protein catabolism is decreased. In some embodiments, the present invention provides methods of decreasing lipid content in the heart of a subject, comprising: administering to said subject an effective amount of a krill oil composition under conditions such that lipid content in the heart of the subject is decreased. In some embodiments, the present invention provides methods of decreasing lipid content in the liver of a subject, comprising: administering to said subject an effective amount of a krill oil composition under conditions such that lipid content in the liver of the subject is decreased.

DEFINITIONS

Figure 1:
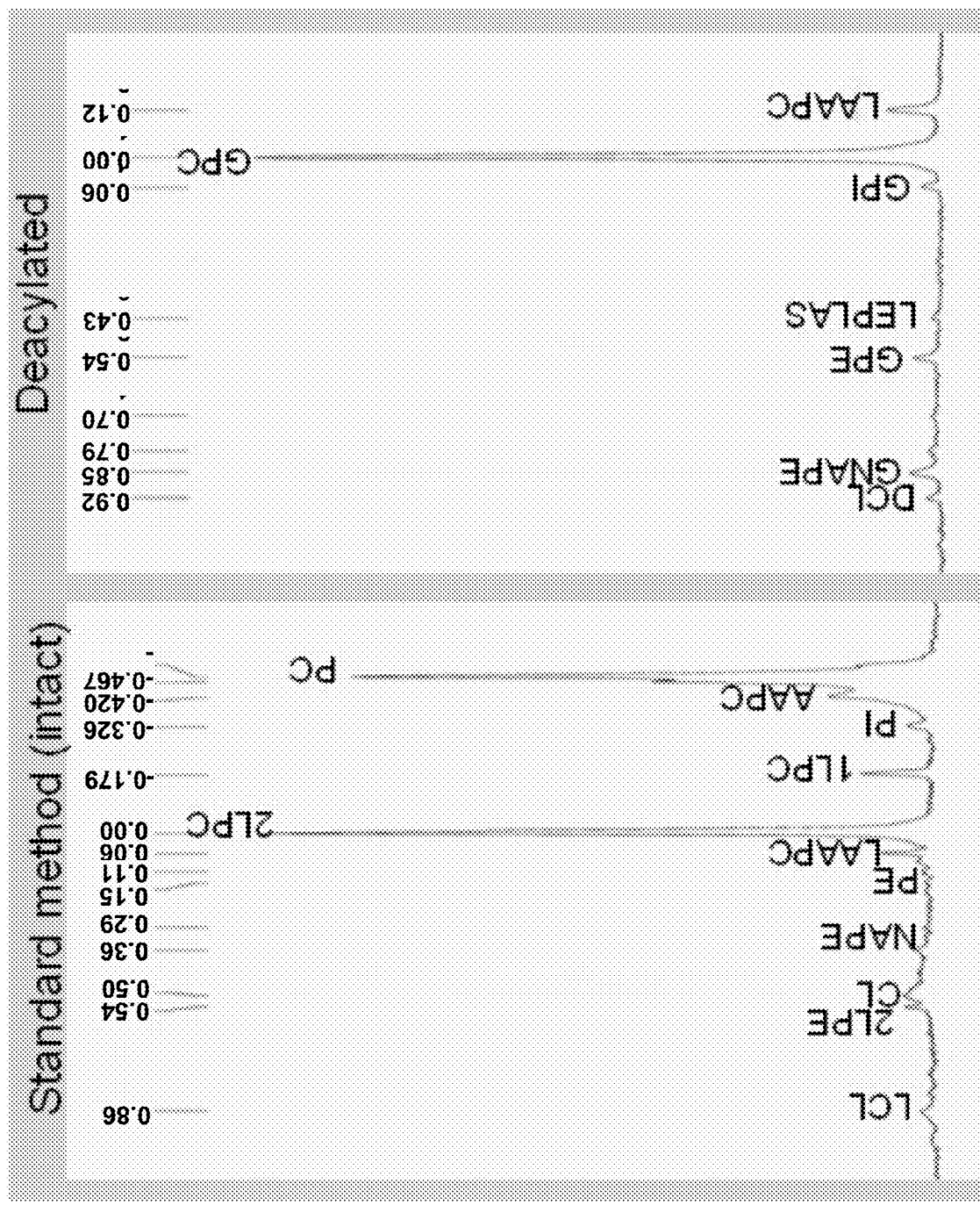
FIG. 1. 31P NMR analysis of polar lipids in krill oil.
Figure 2:
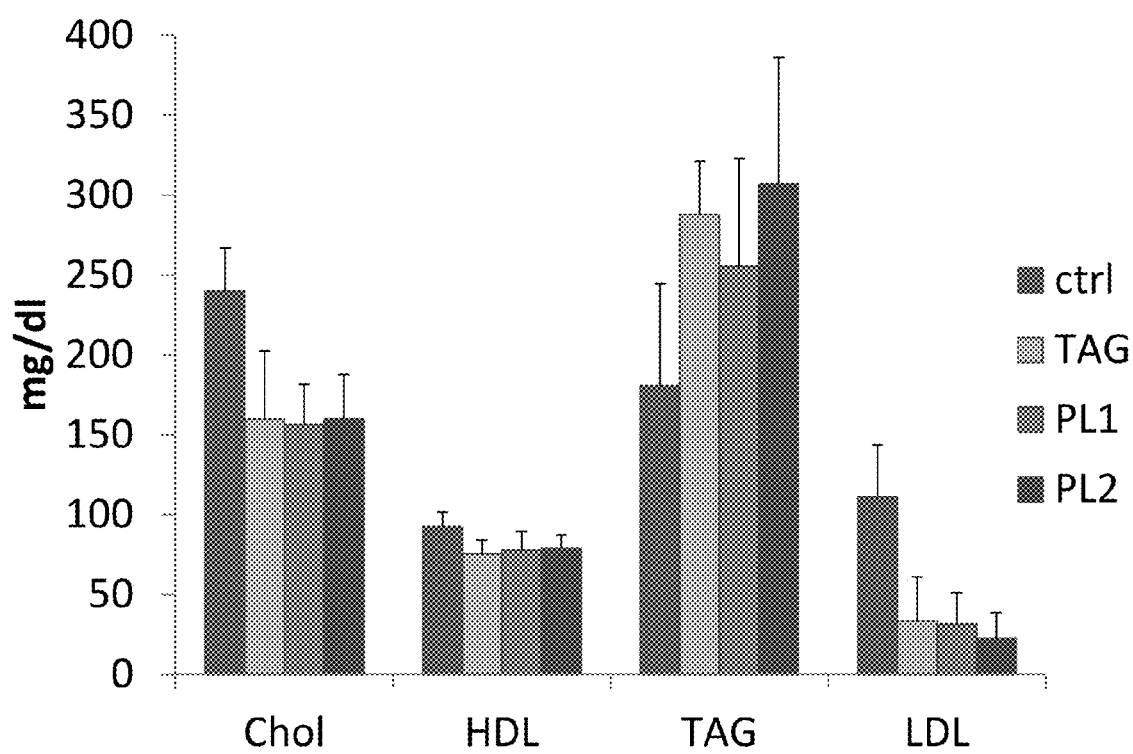
FIG. 2. Blood lipid profiles in Zucker rats fed different forms of omega-3 fatty acids (TAG=FO, PL1=NKO and PL2=Superba).
Figure 3:
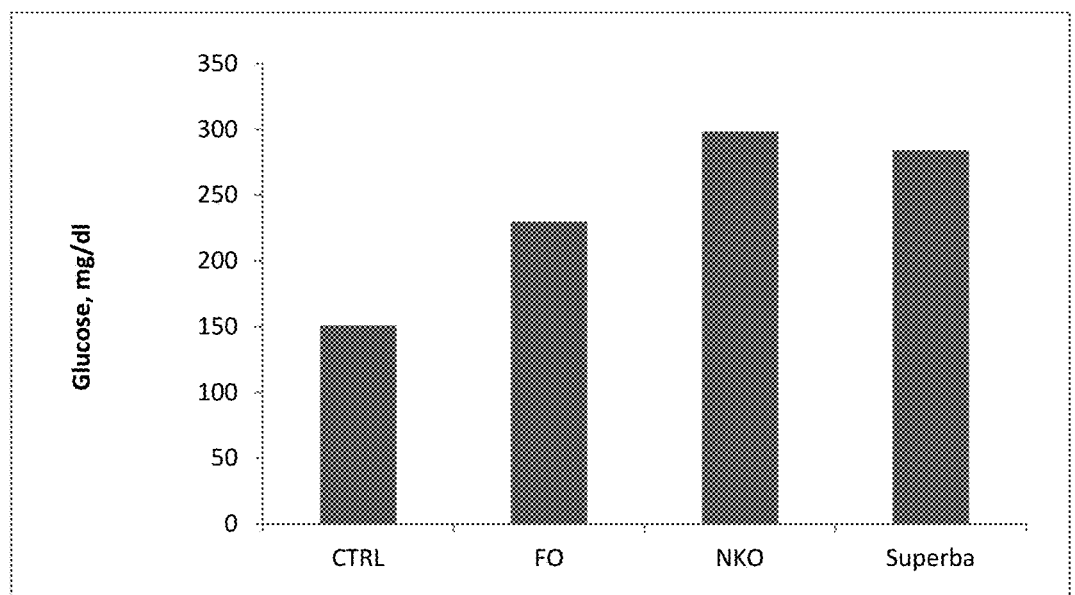
FIG. 3. Plasma glucose concentration in Zucker rats fed different forms of omega-3 fatty acids.
Figure 4:
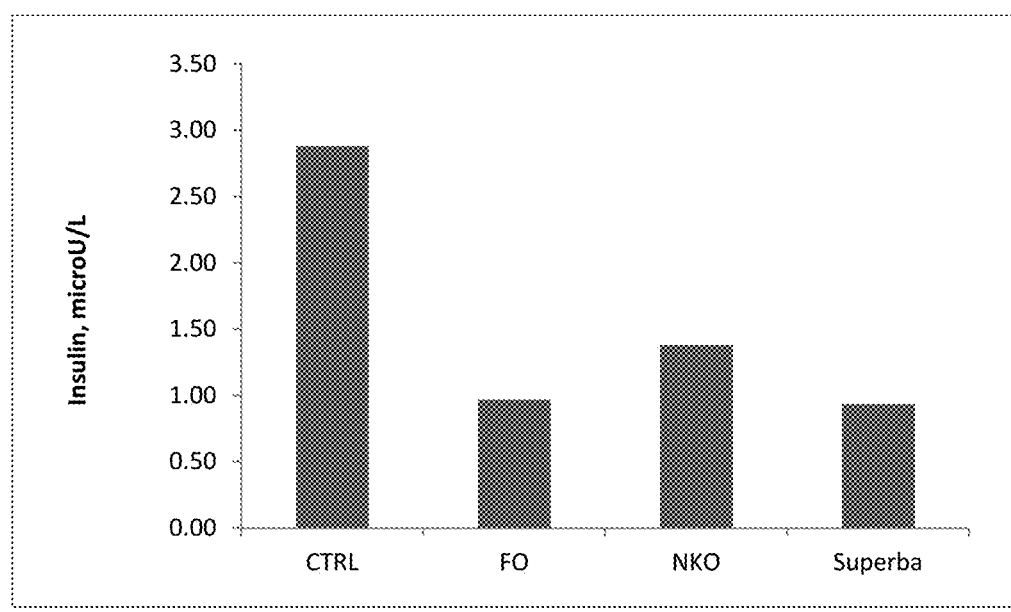
FIG. 4. Plasma insulin concentration in Zucker rats fed different forms of omega-3 fatty acids.
Figure 5:
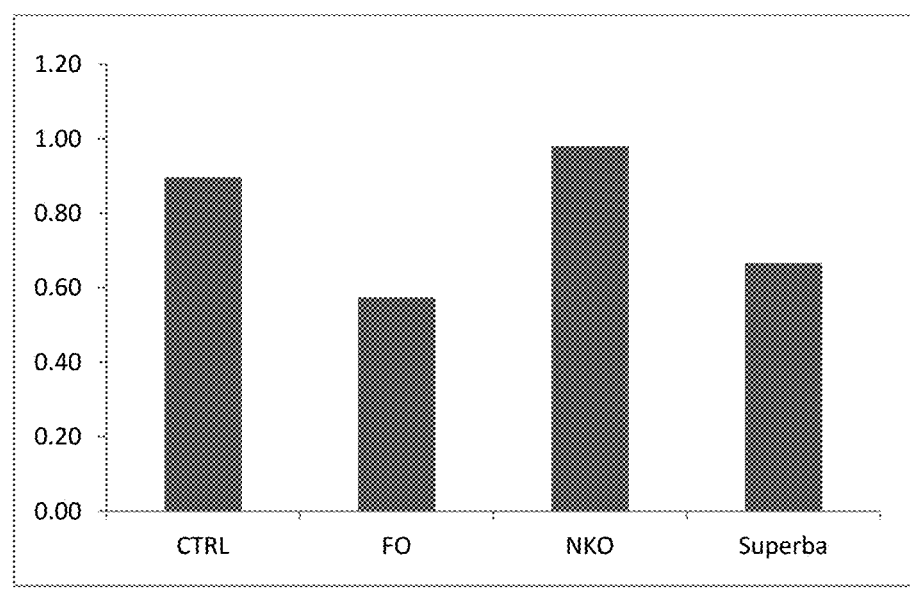
FIG. 5. Estimated HOMA-IR values in Zucker rats fed different forms of omega-3 fatty acids.
Figure 6:
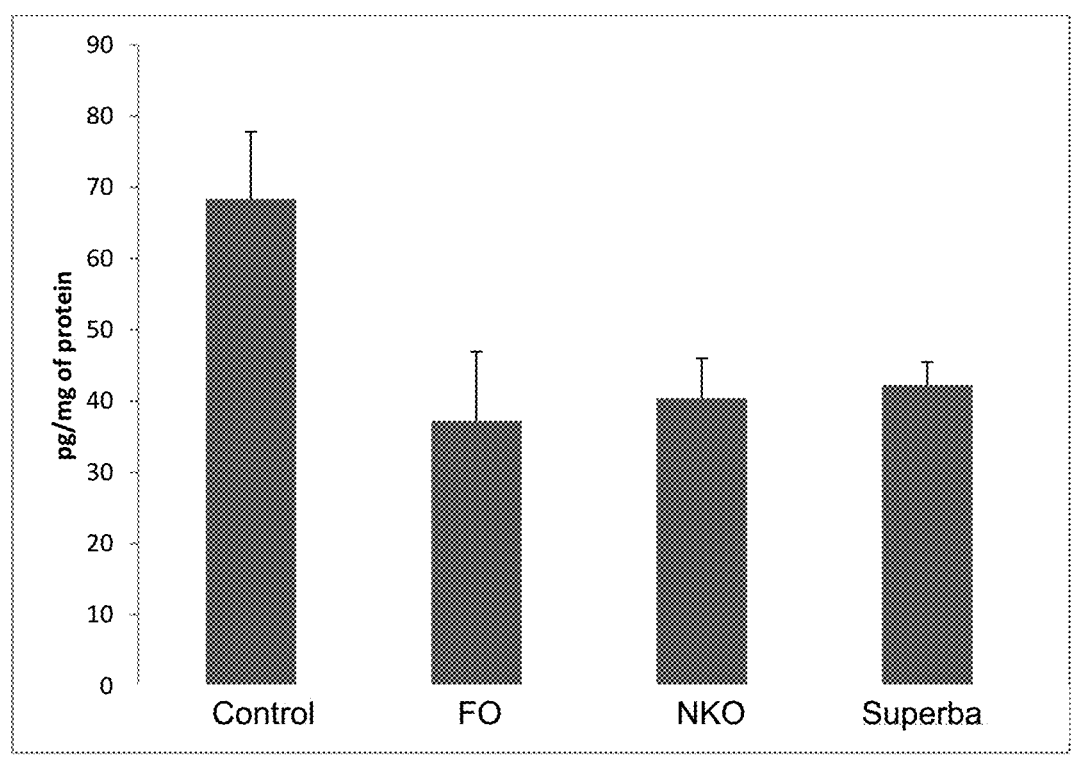
FIG. 6. The effect of dietary omega-3 fatty acids on TNF production by peritoneal macrophages.
Figure 7:
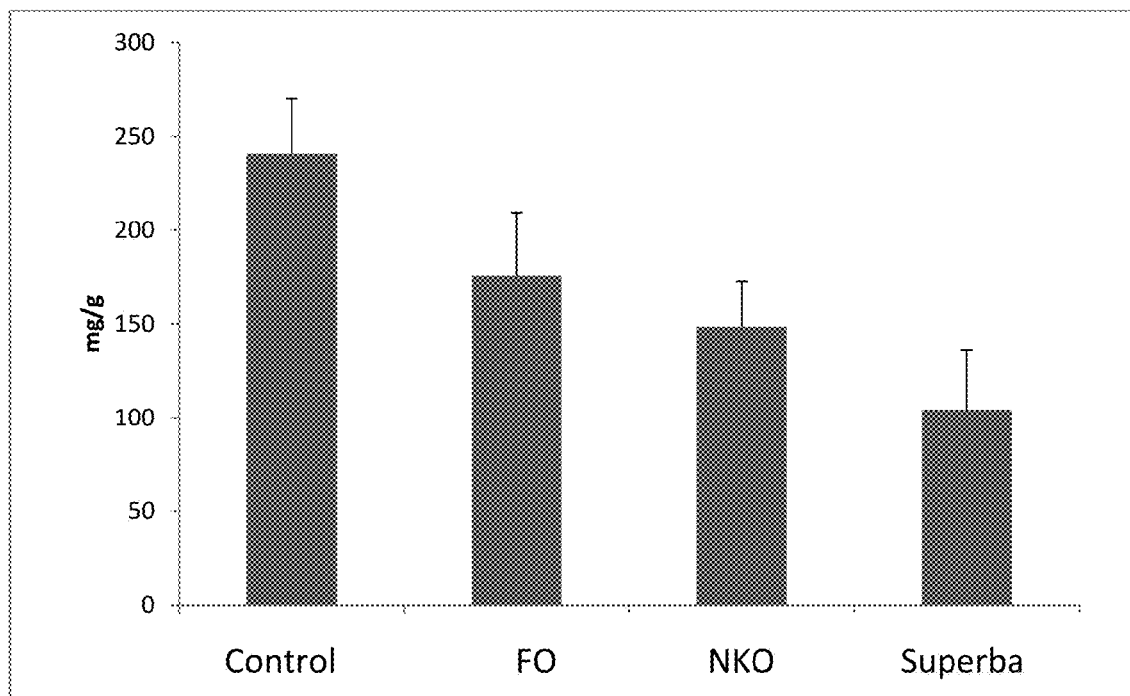
FIG. 7. The effect of dietary omega-3 fatty acids on lipid accumulation in the liver.
Figure 8:
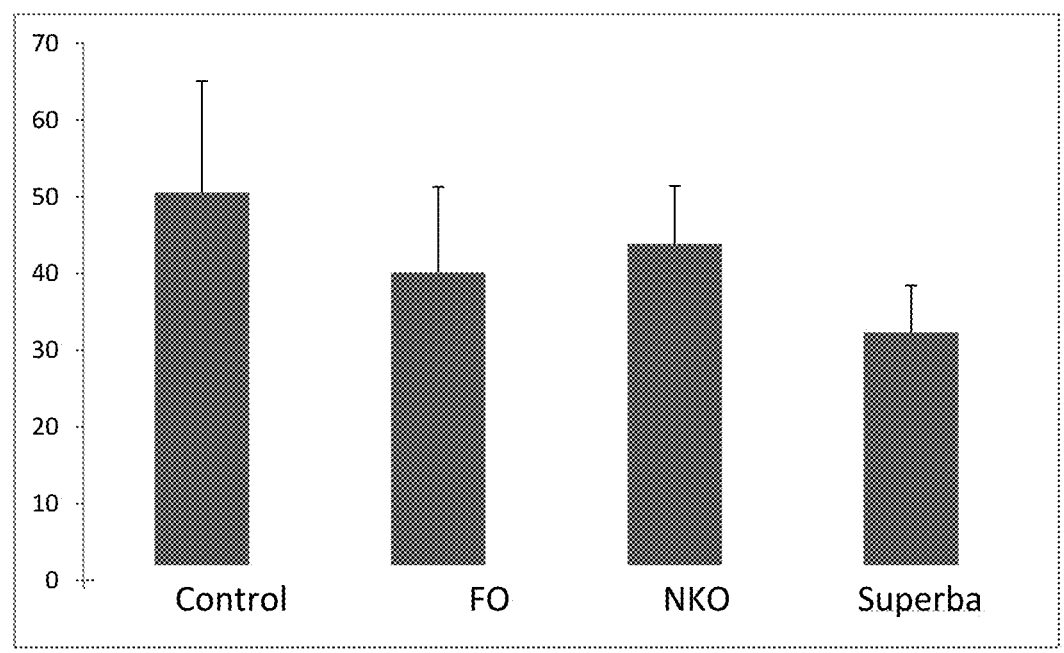
FIG. 8. The effect of dietary omega-3 fatty acids on lipid accumulation in the muscle.
Figure 9:
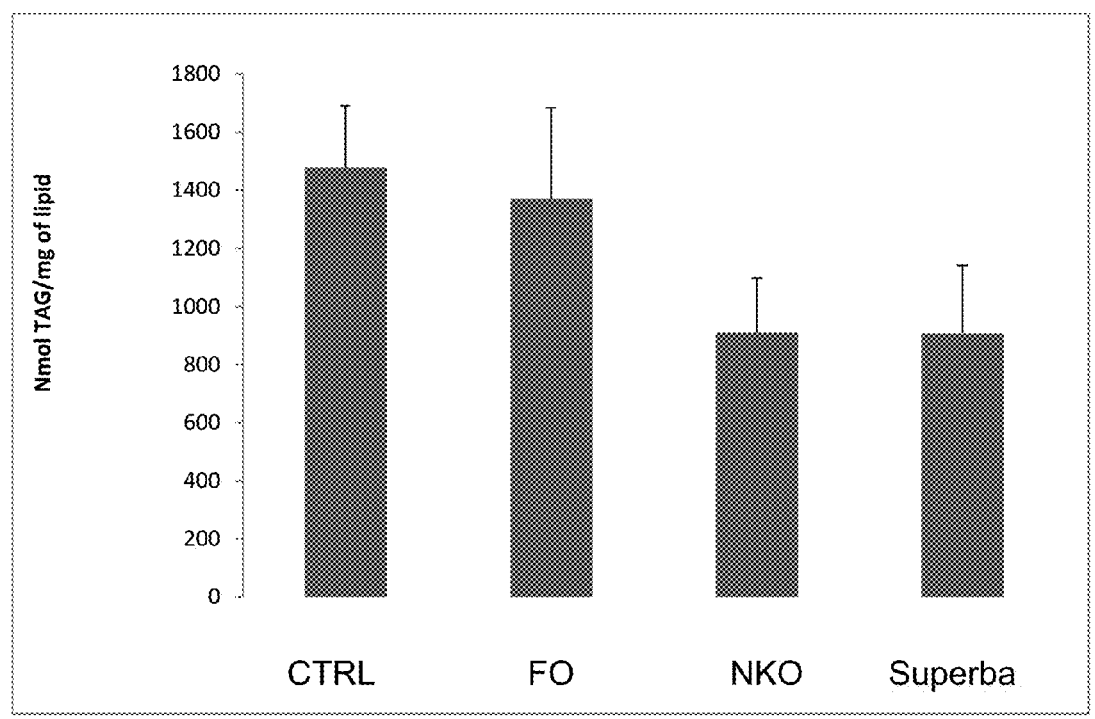
FIG. 9. The effect of dietary omega-3 fatty acids on lipid accumulation in the heart.

As used herein, "phospholipid" refers to an organic compound having the following general structure:

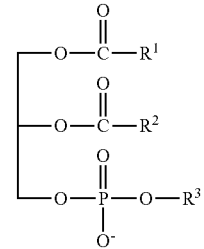

wherein R1 is a fatty acid residue, R2 is a fatty acid residue or —OH, and R3 is a —H or nitrogen containing compound choline (HOCH$_2$CH$_2$N$^+$(CH$_3$)$_3$OH$^-$), ethanolamine (HOCH$_2$CH$_2$NH$_2$), inositol or serine. R1 and R2 cannot simultaneously be OH. When R3 is an —OH, the compound is a diacylglycerophosphate, while when R3 is a nitrogen-containing compound, the compound is a phosphatide such as lecithin, cephalin, phosphatidyl serine or plasmalogen.

An "ether phospholipid" as used herein refers to a phospholipid having an ether bond at position 1 the glycerol backbone. Examples of ether phospholipids include, but are not limited to, alkylacylphosphatidylcholine (AAPC), lyso-alkylacylphosphatidylcholine (LAAPC), and alkylacylphosphatidylethanolamine (AAPE). A "non-ether phospholipid" is a phospholipid that does not have an ether bond at position 1 of the glycerol backbone.

As used herein, the term omega-3 fatty acid refers to polyunsaturated fatty acids that have the final double bond in the hydrocarbon chain between the third and fourth carbon atoms from the methyl end of the molecule. Non-limiting examples of omega-3 fatty acids include, 5,8,11,14,17-eicosapentaenoic acid (EPA), 4,7,10,13,16,19-docosahexanoic acid (DHA) and 7,10,13,16,19-docosapentanoic acid (DPA).

As used herein, astaxanthin refers to the following chemical structure:

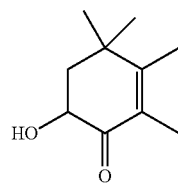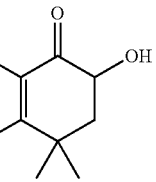

As used herein, astaxanthin esters refer to the fatty acids esterified to OH group in the astaxanthin molecule.

As used herein, the term w/w (weight/weight) refers to the amount of a given substance in a composition on weight basis. For example, a composition comprising 50% w/w phospholipids means that the mass of the phospholipids is 50% of the total mass of the composition (i.e., 50 grams of phospholipids in 100 grams of the composition, such as an oil).

DETAILED DESCRIPTION OF THE INVENTION

This invention discloses novel krill oil compositions characterized by containing high levels of astaxanthin, phospholipids, included an enriched quantities of ether phospholipids, and omega-3 fatty acids. The krill oils compositions are extracted from krill meal using supercritical fluid extraction (SFE) with a co-solvent modifier. The krill meal has been processed on board a ship in Antarctica using live krill as starting material in order to ensure the highest possible quality of the krill meal. The krill oils are extracted from the krill meal in two stages, in step 1 the neutral fraction is extracted using neat supercritical $CO_2$ or in combination with 5% ethanol. The neutral fraction consisted mostly of triglycerides and cholesterol. In stage 2, the polar lipids (phospholipids) are extracted by adding at least 20% ethanol to the supercritical $CO_2$ extraction medium.

The present invention provides methods to avoid decomposition of glycerides and phospholipids in krill oil and compositions produced by those methods. The product obtained by these new methods is virtually free of enzymatically decomposed oil constituents. The solution to the problem is to incorporate a protein denaturation step on fresh krill prior to use of any extraction technology. Denaturation can be achieved by thermal stress or by other means. After denaturation, the oil can be extracted by an optional selection of nonpolar and polar solvents including use of supercritical carbon dioxide. Krill is adapted to a very efficient nutrient digestion at very low temperatures. Therefore the enzymes are sensitive to heat and the step of applying thermal denaturation of lipases and phospholipases does not imply use of very high temperatures. Surprisingly, it has been found that the use of mild denaturation conditions can greatly enhance the quality of krill oil.

Additionally, a major obstacle of several processes of extraction is the cost of removing water. This is particularly true for methods feasible for extraction of highly unsaturated lipids where freeze drying has been regarded as the method of choice to avoid oxidative breakdown of lipids. However, the lipids in krill are surprisingly stable against oxidative deterioration. Therefore, a process including moderate use of heat in the water removing process is feasible provided that the enzymes have been inactivated.

A. Krill Processing

The present invention provides methods for processing freshly caught krill at the site of capture and preferably on board a ship. After processing on board, the krill can be further subjected to extraction processes on board the ship or at a remote location away from the ship. The processing steps described herein also allow for the storage of krill material, preferably a krill meal for from about 1, 2, 3, 4, 5, 6, 8, 9, 10, 11, or 12 months to about 24 to 36 months prior to processing.

In some preferred embodiments, freshly caught krill is first subjected to a protein denaturation step. The present invention is not limited to any particular method of protein denaturation. In some embodiments, the denaturation is accomplished by application of chemicals, heat, or combinations thereof. In some embodiments, freshly caught krill is wet pressed to obtain oil and meal. In some embodiments, the meal is then heated to a temperature of about 50° C. to about 100° C. for about 20 minutes to about an hour, preferably about 40 minutes to denature the proteins. In some embodiments, this material is then pressed to yield a press cake. When this method is used on krill, only a small amount of oil is released. Most of the oil is still present in the denatured meal. In some embodiments, antioxidants such as ethoxyquin or Vitamin E are added to the meal. However, as shown in the examples, the resulting meal is surprisingly stable. The stability can only partly be explained by addition of an antioxidant to the meal. This antioxidant can, after extraction of the oil from denatured meal, be removed by further processing steps. Alternatively the oil can be extracted rather shortly after production of the meal without any addition of antioxidant in the process. Further, storage conditions at a low to very low temperature can be applied if addition of antioxidant is not desired.

Krill oil extracted from denatured krill meal by supercritical fluid extraction even 19 months after the production of the meal contained virtually no decomposed phospholipids. This product turned out to be substantially different from samples of krill oil available in the market today. Previously described commercial krill processing procedures utilize krill that has been frozen immediately after catching followed by freeze drying and extraction at low temperatures. However, these processes only yield a suitable product if the time the krill is kept frozen is very short or the temperature is extremely low (−60° to −80° C.). However, data provided herein clearly shows that if a step of denaturation of the proteins is added in front of an optional extraction method, an excellent krill oil can be produced even after a long time of storage. This methodology also opens up for use of alternative methods to remove water prior to extraction, which in turn has a great impact on costs in full scale operation. If a long time of storage is desired, the denatured material should preferably be stored at low temperature preferably at −20° C.

In some embodiments, krill oil is extracted from the denatured krill meal. In some embodiments, the krill oil is extracted by contacting the krill meal with ethanol. In some embodiments, krill is then extracted with a ketone solvent such as acetone. In other embodiments, the krill oil is extracted by one or two step supercritical fluid extraction. In some embodiments, the supercritical fluid extraction uses carbon dioxide and neutral krill oil is produced. In some embodiments, the supercritical fluid extraction uses carbon dioxide with the addition of a polar entrainer, such as ethanol, to produce a polar krill oil. In some embodiments, the krill meal is first extracted with carbon dioxide followed by carbon dioxide with a polar entrainer, or vice versa. In some embodiments, the krill meal is first extracted with $CO_2$ supplemented with a low amount of a polar co-solvent (e.g., from about 1% to about 10%, preferably about 5%) such a $C_1$-$C_3$ monohydric alcohol, preferably ethanol, followed by extraction with $CO_2$ supplemented with a high amount of a polar co-solvent (from about 10% to about 30%, preferably about 23%) such as such a $C_1$-$C_3$ monohydric alcohol, preferably ethanol, or vice versa. Surprisingly, it has been found that use of a low amount of polar solvent in the $CO_2$ as an entrainer facilitates the extraction of neutral lipid components and astaxanthin in a single step. Use of the high of polar solvent as an entrainer in the other step facilitates extraction of ether phospholipids, as well as non-ether phospholipids.

The present invention is distinguished from previously described krill oil products, such as those described in U.S. Pat. No. 6,800,299 or WO 03/011873 and Neptune brand krill oil, by having substantially higher levels of non-ether phospholipids, ether phospholipids, and astaxanthin. The krill oils of the present invention also have unexpected and superior properties as compared to previously available krill oils. In particular, the krill oil of the present invention has been demonstrated to reduce blood LDL cholesterol levels, improve DHA transfer to the brain as well as reduce lipid accumulation in the liver and muscle while the previously described krill oil compositions do not have such a properties. Accordingly, in some embodiments, the present invention provides a krill oil composition, preferably a *Euphausia superba* krill oil composition, comprising from about 40% to about 60% w/w phospholipids, preferably from about 45% to 55% w/w phospholipids and from about 300 mg/kg astaxanthin to about 2500 mg/kg astaxanthin, preferably from about 1000 to about 2200 mg/kg astaxanthin, more preferably from about 1500 to about 2200 mg/kg astaxanthin. In some preferred embodiments, the compositions comprise greater than about 1000, 1500, 1800, 1900, 2000, or 2100 mg/kg astaxanthin. In some preferred embodiments, the krill oil compositions of the present invention comprise from about 1%, 2%, 3% or 4% to about 8%, 10%, 12% or 15% w/w ether phospholipids or greater than about 4%, 5%, 6%, 7%, 8%, 9% or 10% ether phospholipids. In some embodiments the ether phospholipids are preferably alkylacylphosphatidylcholine, lyso-alkylacylphosphatidylcholine, alkylacylphosphatidyl-ethanolamine or combinations thereof. In some embodiments, the krill oil compositions comprise from about 1%, 2%, 3% or 4% to about 8%, 10%, 12% or 15% w/w ether phospholipids and from about 30%, 33%, 40%, 42%, 45%, 48%, 50%, 52%, 54%, 55% 56%, 58% to about 60% non-ether phospholipids so that the total amount of phospholipids (both ether and non-ether phospholipids) ranges from about 40% to about 60%. One of skill in the art will recognize that the range of 40% to 60% total phospholipids, as well as the other ranges of ether and non-ether phospholipids, can include other values not specifically listed within the range.

In further embodiments, the compositions comprise from about 20% to 45% w/w triglycerides; and from about 400 to about 2500 mg/kg astaxanthin. In some embodiments, the compositions comprise from about 20% to 35%, preferably from about 25% to 35%, omega-3 fatty acids as a percentage of total fatty acids in the composition, wherein from about 70% to 95%, or preferably from about 80% to 90% of the omega-3 fatty acids are attached to the phospholipids. In some embodiments, the present invention provides encapsulated *Euphausia superba* krill oil compositions. In some embodiments, the present invention provides a method of making a *Euphausia superba* krill oil composition comprising contacting *Euphausia superba* with a polar solvent to provide an polar extract comprising phospholipids, contacting *Euphausia superba* with a neutral solvent to provide a neutral extract comprising triglycerides and astaxanthin, and combining said polar extract and said neutral extract to provide the *Euphausia superba* krill oils described above. In some embodiments, fractions from polar and non-polar extractions are combined to provide a final product comprising the desired ether phospholipids, non-ether phospholipids, omega-3 moieties and astaxanthin. In other embodiments, the present invention provides methods of making a *Euphausia superba* (or other krill species) krill oil comprising contacting a *Euphausia superba* preparation such as *Euphausia superba* krill meal under supercritical conditions with $CO_2$ containing a low amount of a polar solvent such as ethanol to extract neutral lipids and astaxanthin; contacting meal remaining from the first extraction step under supercritical conditions with $CO_2$ containing a high amount of a polar solvent such as ethanol to extract a polar lipid fraction containing ether and non-ether phospholipids; and then blending the neutral and polar lipid extracts to provide the compositions described above.

The krill oil extracted by the methods of the present invention contains few enzymatic breakdown products. Examples of the krill oil compositions of the present invention are provided in Tables 9-24. In some embodiments, the present invention provides a polar krill oil comprising at least 65% (w/w) of phospholipids, wherein the phospholipids are characterized in containing at least 35% omega-3 fatty acid residues. The present invention is not limited to the presence of any particular omega-3 fatty acid residues in the krill oil composition. In some preferred embodiments, the krill oil comprises EPA and DHA residues. In some embodiments, the krill oil compositions comprise less than about 5%, 4%, 3% or preferably 2% free fatty acids on a weight/weight (w/w) basis. In some embodiments, the krill oil compositions comprise less than about 25%, 20%, 15%, 10% or 5% triglycerides (w/w). In some embodiments, the krill oil compositions comprise greater than about 30%, 40%, 45%, 50%, 55%, 60%, or 65% phosphatidyl choline (w/w). In some embodiments, the krill oil compositions comprise greater than about 100, 200, 300, 400, or 500 mg/kg astaxanthin esters and up to about 700 mg/kg astaxanthin esters. In some embodiments, the present invention provides krill oil compositions comprising at least 500, 1000, 1500, 2000, 2100, or 2200 mg/kg astaxanthin esters and at least 36% (w/w) omega-3 fatty acids. In some embodiments, the krill oil compositions of the present invention comprise less than about 1.0 g/100 g, 0.5 g/100 g, 0.2 g/100 g or 0.1 g/100 g total cholesterol. In some embodiments, the krill oil compositions of the present invention comprise less than about 0.45

In some embodiments, the present invention provides a neutral krill oil extract comprising greater than about 70%, 75% 80%, 85% or 90% triglycerides. In some embodiments, the krill oil compositions comprise from about 50 to about 2500 mg/kg astaxanthin esters. In some embodiments, the krill oil compositions comprise from about 50, 100, 200, or 500 to about 750, 1000, 1500 or 2500 mg/kg astaxanthin esters. In some embodiments, the compositions comprise from about 1% to about 30% omega-3 fatty acid residues, and preferably from about 5%-15% omega-3 fatty acid residues. In some embodiments, the krill oil compositions comprise less than about 20%, 15%, 10% or 5% phospholipids.

In some embodiments, the present invention provides krill oil containing less than about 70, 60, 50, 40, 30, 20, 10, 5 or 1 micrograms/kilogram (w/w) astaxanthin esters. In some embodiments, the krill oil is clear or only has a pale red color. In some embodiments, the low-astaxanthin krill oil is obtained by first extracting a krill material, such as krill oil, by supercritical fluid extraction with neat carbon dioxide. It is contemplated that this step removes astaxanthin from the krill material. In some embodiments, the krill material is then subjected to supercritical fluid extraction with carbon dioxide and a polar entrainer such as ethanol, preferably about 20% ethanol. The oil extracted during this step is characterized in containing low amounts of astaxanthin. In other embodiments, krill oil comprising astaxanthin is extracted by countercurrent supercritical fluid extraction with neat carbon dioxide to provide a low-astaxanthin krill oil.

In some embodiments, the present invention provides krill oil that is substantially odorless. By substantially odorless it is meant that the krill oil lacks an appreciable odor as determined by a test panel. In some embodiments, the substantially odorless krill oil comprises less than about 10, 5 or 1 milligrams/kilogram trimethylamine. In some preferred embodiments, the odorless krill oil is produced by first subjecting krill material to supercritical fluid extraction with neat carbon dioxide to remove odor causing compounds such as trimethylamine, followed by extraction with carbon dioxide with a polar entrainer such as ethanol.

In some embodiments, the present invention provides a delipidated krill meal produced after extraction of lipids from the krill meal. In some embodiments, the delipidated krill meal comprises krill protein. In some embodiments, the delipidated krill meal comprises less than about 200, 150, 120, 100, 75, 65, 60, 55, or 50 g/kg total fat. In some embodiments, the delipidated krill meal comprises from about 1 to about 100 mg/kg astaxanthin esters, and preferably from about 5 to about 20 mg/kg astaxanthin esters. In some embodiments, the delipidated krill meal comprises greater than about 60%, 65%, 70% or 75% krill protein. In some embodiments, the present invention provides animal feeds comprising the delipidated krill meal. In some embodiments, the animal feed is a fish feed or aquatic organism feed, such as shrimp feed, crab feed, or crawfish feed. In preferred embodiments, the krill meal is incorporated into complete ration for the target organism. In preferred embodiments, the feed is provided in pelleted form. In many instances, compounds such as astaxanthin are removed during delipidation. The methods of the present invention provide a delipidated krill meal that retains significant amounts of astaxanthin. Accordingly, in some embodiments, the present invention provides methods of feeding aquatic organisms, comprising providing to the aquatic organism a feed comprising the delipidated krill meal described above. In other embodiments, the present invention provides methods of increasing flesh coloration in an aquatic species comprising feeding the aquatic species a comprising the delipidated krill meal described above.

B. Compositions Containing Krill Oil

In some embodiments, the compositions of this invention (such as those described in the preceding sections) are contained in acceptable excipients and/or carriers for oral consumption. The actual form of the carrier, and thus, the composition itself, is not critical. The carrier may be a liquid, gel, gelcap, capsule, powder, solid tablet (coated or non-coated), tea, or the like. The composition is preferably in the form of a tablet or capsule and most preferably in the form of a soft gel capsule. Suitable excipient and/or carriers include maltodextrin, calcium carbonate, dicalcium phosphate, tricalcium phosphate, microcrystalline cellulose, dextrose, rice flour, magnesium stearate, stearic acid, croscarmellose sodium, sodium starch glycolate, crospovidone, sucrose, vegetable gums, lactose, methylcellulose, povidone, carboxymethylcellulose, corn starch, and the like (including mixtures thereof). Preferred carriers include calcium carbonate, magnesium stearate, maltodextrin, and mixtures thereof. The various ingredients and the excipient and/or carrier are mixed and formed into the desired form using conventional techniques. The tablet or capsule of the present invention may be coated with an enteric coating that dissolves at a pH of about 6.0 to 7.0. A suitable enteric coating that dissolves in the small intestine but not in the stomach is cellulose acetate phthalate. Further details on techniques for formulation for and administration may be found in the latest edition of Remington's Pharmaceutical Sciences (Maack Publishing Co., Easton, Pa.).

The dietary supplement may comprise one or more inert ingredients, especially if it is desirable to limit the number of calories added to the diet by the dietary supplement. For example, the dietary supplement of the present invention may also contain optional ingredients including, for example, herbs, vitamins, minerals, enhancers, colorants, sweeteners, flavorants, inert ingredients, and the like. For example, the dietary supplement of the present invention may contain one or more of the following: ascorbates (ascorbic acid, mineral ascorbate salts, rose hips, acerola, and the like), dehydroepiandosterone (DHEA), Fo-Ti or Ho Shu Wu (herb common to traditional Asian treatments), Cat's Claw (ancient herbal ingredient), green tea (polyphenols), inositol, kelp, dulse, bioflavinoids, maltodextrin, nettles, niacin, niacinamide, rosemary, selenium, silica (silicon dioxide, silica gel, horsetail, shavegrass, and the like), spirulina, zinc, and the like. Such optional ingredients may be either naturally occurring or concentrated forms.

In some embodiments, the dietary supplements further comprise vitamins and minerals including, but not limited to, calcium phosphate or acetate, tribasic; potassium phosphate, dibasic; magnesium sulfate or oxide; salt (sodium chloride); potassium chloride or acetate; ascorbic acid; ferric orthophosphate; niacinamide; zinc sulfate or oxide; calcium pantothenate; copper gluconate; riboflavin; beta-carotene; pyridoxine hydrochloride; thiamin mononitrate; folic acid; biotin; chromium chloride or picolonate; potassium iodide; sodium selenate; sodium molybdate; phylloquinone; vitamin D3; cyanocobalamin; sodium selenite; copper sulfate; vitamin A; vitamin C; inositol; potassium iodide. Suitable dosages for vitamins and minerals may be obtained, for example, by consulting the U.S. RDA guidelines.

In further embodiments, the compositions comprise at least one food flavoring such as acetaldehyde (ethanal), acetoin (acetyl methylcarbinol), anethole (parapropenyl anisole), benzaldehyde (benzoic aldehyde), N butyric acid (butanoic acid), d or 1 carvone (carvol), cinnamaldehyde (cinnamic aldehyde), citral (2,6 dimethyloctadien 2,6 al 8, gera nial, neral), decanal (N decylaldehyde, capraldehyde, capric aldehyde, caprinaldehyde, aldehyde C 10), ethyl acetate, ethyl butyrate, 3 methyl 3 phenyl glycidic acid ethyl ester (ethyl methyl phenyl glycidate, strawberry aldehyde, C 16 aldehyde), ethyl vanillin, geraniol (3,7 dimethyl 2,6 and 3,6 octadien 1 ol), geranyl acetate (geraniol acetate), limonene (d, 1, and dl), linalool (linalol, 3,7 dimethyl 1,6 octadien 3 ol), linalyl acetate (bergamol), methyl anthranilate (methyl 2 aminobenzoate), piperonal (3,4 methylenedioxy benzaldehyde, heliotropin), vanillin, alfalfa (*Medicago sativa* L.), allspice (*Pimenta officinalis*), ambrette seed (*Hibiscus abelmoschus*), angelic (*Angelica archangelica*), Angostura (*Galipea officinalis*), anise (*Pimpinella anisum*), star anise (*Illicium verum*), balm (*Melissa officinalis*), basil (*Ocimum basilicum*), bay (*Laurus nobilis*), calendula (*Calendula officinalis*), (*Anthemis nobilis*), capsicum (*Capsicum frutescens*), caraway (*Carum carvi*), cardamom (*Elettaria cardamomum*), cassia, (*Cinnamomum cassia*), cayenne pepper (*Capsicum frutescens*), Celery seed (*Apium graveolens*), chervil (*Anthriscus cerefolium*), chives (*Allium schoenoprasum*), coriander (*Coriandrum sativum*), cumin (*Cuminum cyminum*), elder flowers (*Sambucus canadensis*), fennel (*Foeniculum vulgare*), fenugreek (*Trigonella foenum graecum*), ginger (*Zingiber officinale*), horehound (*Marrubium vulgare*), horseradish (*Armoracia lapathifolia*), hyssop (*Hyssopus officinalis*), lavender (*Lavandula officinalis*), mace (*Myristica fragrans*), marjoram (*Majorana hortensis*), mustard (*Brassica nigra, Brassica juncea, Brassica hirta*), nutmeg (*Myristica fragrans*), paprika (*Capsicum annuum*), black pepper (*Piper nigrum*), peppermint (*Mentha piperita*), poppy seed (*Papaver somniferum*), rosemary (*Rosmarinus officinalis*), saffron (*Crocus sativus*), sage (*Salvia officinalis*), savory (*Satureia hortensis, Satureia montana*), sesame (*Sesamum indicum*), spearmint (*Mentha spicata*), tarragon (*Artemisia dracunculus*), thyme (*Thymus vulgaris, Thymus serpyllum*), turmeric (*Curcuma longa*), vanilla (*Vanilla planifolia*), zedoary (*Curcuma zedoaria*), sucrose, glucose, saccharin, sorbitol, mannitol, aspartame. Other suitable flavoring are disclosed in such references as Remington's Pharmaceutical Sciences, 18th Edition, Mack Publishing, p. 1288-1300 (1990), and Furia and Pellanca, Fenaroli's Handbook of Flavor Ingredients, The Chemical Rubber Company, Cleveland, Ohio, (1971), known to those skilled in the art.

In other embodiments, the compositions comprise at least one synthetic or natural food coloring (e.g., annatto extract, astaxanthin, beet powder, ultramarine blue, canthaxanthin, caramel, carotenal, beta carotene, carmine, toasted cottonseed flour, ferrous gluconate, ferrous lactate, grape color extract, grape skin extract, iron oxide, fruit juice, vegetable juice, dried algae meal, tagetes meal, carrot oil, corn endosperm oil, paprika, paprika oleoresin, riboflavin, saffron, tumeric, tumeric and oleoresin).

In still further embodiments, the compositions comprise at least one phytonutrient (e.g., soy isoflavonoids, oligomeric proanthcyanidins, indol 3 carbinol, sulforaphone, fibrous ligands, plant phytosterols, ferulic acid, anthocyanocides, triterpenes, omega 3/6 fatty acids, conjugated fatty acids such as conjugated linoleic acid and conjugated linolenic acid, polyacetylene, quinones, terpenes, cathechins, gallates, and quercitin). Sources of plant phytonutrients include, but are not limited to, soy lecithin, soy isoflavones, brown rice germ, royal jelly, bee propolis, acerola berry juice powder, Japanese green tea, grape seed extract, grape skin extract, carrot juice, bilberry, flaxseed meal, bee pollen, *ginkgo biloba*, primrose (evening primrose oil), red clover, burdock root, dandelion, parsley, rose hips, milk thistle, ginger, Siberian ginseng, rosemary, curcumin, garlic, lycopene, grapefruit seed extract, spinach, and broccoli.

In still other embodiments, the compositions comprise at least one vitamin (e.g., vitamin A, thiamin (B1), riboflavin (B2), pyridoxine (B6), cyanocobalamin (B12), biotin, ascorbic acid (vitamin C), retinoic acid (vitamin D), vitamin E, folic acid and other folates, vitamin K, niacin, and pantothenic acid). In some embodiments, the particles comprise at least one mineral (e.g., sodium, potassium, magnesium, calcium, phosphorus, chlorine, iron, zinc, manganese, flourine, copper, molybdenum, chromium, selenium, and iodine). In some particularly preferred embodiments, a dosage of a plurality of particles includes vitamins or minerals in the range of the recommended daily allowance (RDA) as specified by the United States Department of Agriculture. In still other embodiments, the particles comprise an amino acid supplement formula in which at least one amino acid is included (e.g., 1-carnitine or tryptophan).

C. Uses of Krill Oil

Previously, it was disclosed that omega-3 fatty acids have anti-inflammatory properties. See, e.g., Calder. Am. J. Clin. Nutr. 83 (2006) 1505S. In addition, in it was disclosed that a phospholipid emulsion derived from a marine and/or synthetic origin comprising polyunsaturated fatty acids have anti-inflammatory and/or immuno-suppressive effects. See, e.g., U.S. Pat. No. 5,434,183. An embodiment of this invention is a krill oil composition effective for reducing inflammation i.e. reducing the levels of TNF-α, IL-1 beta, IL-6, IL-10, TGF beta and fibrinogen in the blood.

Type 2 diabetes is a metabolic disorder characterized by impaired glycemic control (high blood glucose levels). In type 2 diabetes, it is the tissue wide insulin resistance that contributes to the development of the disease. Strategies reducing insulin resistance or improving tissue sensitivity to insulin are recognized as beneficial in preventing type 2 diabetes. In healthy humans, a 3-week supplementation with fish oil (1.1 g EPA/d and 0.7 g DHA/d) decreased the insulin response to an oral glucose load by 40%. Omega-3 PUFA dietary enrichment resulted in lower glucose oxidation, higher fat oxidation, and increased glycogen storage; the glycemic response was unchanged, however, which indicates an improved sensitivity to insulin. In another embodiment of this invention is a krill oil composition effective for reducing the insulin resistance.

Krill oil has not been disclosed as being effective in treating one of the most important life style problems of modern societies, i.e., excess weight gain and obesity. Excess adipose tissue mass (overweight and obesity) is associated with low grade inflammation in adipose tissue and in the whole body reflecting the inflammatory mediators "spilling over" from fat tissue. Trayhurn et al., Br. J. Nutrition (2004), 92(3), 347-355. Inflammation appears to be an important link between obesity and metabolic syndrome/type-II diabetes as well as cardiovascular disease. Libby et al., J. Amer. Coll. Card. (2006), 48(9, Suppl. A), A33-A46. Thus, excess adipose tissue is an unhealthy condition. Weight reduction will improve the inflammatory condition, but persistent weight reduction is difficult to achieve. Omega-3 fatty acid supplementation may alleviate the inflammatory condition in adipose tissue and thus ideally complement the principal strategies of weight reduction i.e. low calorie diet and exercise. There are clinical studies in humans that demonstrate that omega-3 enhance the effect of very low calorie diet and exercise in reducing body fat mass. Kunesova et al., Physiological research/Academia Scientiarum Bohemoslovaca (2006), 55(1), 63-72. Although diet and exercise regime may fail to result in consistent decrease in weight in long term, the effect of omega-3 fatty acids alleviating the inflammatory condition in the adipose tissue may persist generating a condition that can be described as "healthy adipose tissue". Previously, it was shown that dietary omega-3 fatty acids can be used to reduce inflammation in adipose tissue without influencing level of obesity. Todoric et al., Diabetologia (2006), 49(9), 2109-2119. Reduction in adipose tissue inflammation was demonstrated by an increase in circulating levels of adiponectin. Adiponectin is an adipose tissue derived anti-inflammatory hormone. Results on the treatment of obese people with omega-3 fatty acids to alleviate circulating levels of inflammatory markers are inconclusive. Trebble et al., Br. J. Nutrition (2003), 90(2), 405-412. However, duration of these studies may not have been sufficient given the slow turnover of adipose tissue in humans. Itoh et al. found that 1.8 g/d of EPA increased adiponectin, a marker of adipose tissue derived inflammation, in a group of overweight subjects with metabolic syndrome. Itoh et al., Arteriosclerosis, Thrombosis, and Vascular Biology (2007), 27(9), 1918-1925.

An embodiment of the invention is the use of krill oil to increase serum adiponectin levels. Adiponectin is a protein hormone that modulates a number of metabolic processes, including glucose regulation and fatty acid catabolism. Adiponectin is exclusively secreted from adipose tissue into the bloodstream and is very abundant in plasma relative to many hormones. Levels of the hormone are inversely correlated with body mass index (BMI). The hormone plays a role in alleviating the metabolic dysregulation that may result in type 2 diabetes, obesity, atherosclerosis and non-alcoholic fatty liver disease (NAFLD). Diez et al., Eur. J. Endocrinol. 148 (3): 293-300; Ukkola et al., J. Mol. Med. 80 (11): 696-702.

Another embodiment of the invention is to use krill oil in an overweight and obese subjects for alleviating diet induced adipose tissue dysfunction and diet induced changes in the lipid metabolism.

In further embodiments, krill oil is effective in reducing risk factors of type 2 diabetes such as hyperinsulinemia and insulin resistance and cardiovascular disease risk factors in overweight subjects. In addition this invention discloses that krill oil is effective in preventing accumulation of fat in muscles and in the liver (liver steatosis).

It is well known in the art that the obese Zucker rat is a useful rat model to study metabolic Syndrome X and non-insulin dependent diabetes mellitus, including glucose tolerance, insulin resistance and hyperinsulinaemia. It has also been shown previously that astaxanthin is a powerful antioxidant, useful for prevention of oxidative stress in vivo and in Zucker rats using vitamin E. See, e.g., Aoi et al., (2003). Antioxidants & Redox Signaling. 5(1):139-44; Laight et al., Eur. J. Pharmacol. 377 (1999) 89.

In yet another embodiment of the invention is a krill oil composition effective of improving the blood lipid profile by increasing the HDL cholesterol levels, decreasing the LDL cholesterol and triglyceride levels. Hence the novel krill oil composition is effective for treating metabolic syndrome. Metabolic syndrome is defined as the coexistence of 3 or more components selected from the group: abdominal obesity, high serum triglyceride levels, low HDL levels, elevated blood pressure and high fasting plasma glucose levels.

In another embodiment of the invention, the krill oil compositions are found to be effective and safe for the treatment of metabolic syndrome in humans.

In still other embodiments, the krill oil compositions of the present invention find use in increasing or inducing diuresis. In some embodiments, the krill oil compositions of the present invention find use in decreasing protein catabolism and increasing the muscle mass of a subject.

In some embodiments, the kill oil composition of the present invention find use in the treatment of fatty heart disease and non-alcoholic fatty acid liver disease. Thus, the krill oil compositions are useful for decreasing the lipid content of the heart and/or liver and/or muscle of a subject.

In yet another embodiment of the invention is a method to increase the transfer of DHA to the brain.

Example 1

Antarctic krill (*Euphausia superba*) was captured and brought on board alive, before it was processed into krill meal, an oil (asta oil) and stickwater. The composition and properties of the krill meal was monitored during the processing and compared to a commercial competitor (Table 1 and 2). Furthermore, the amino acid composition of the krill meal and stickwater was determined (Table 3), showing that krill meal is a suitable feed source for to be used in aquaculture due to the presences of all the essential amino acids teleost fish require. During the krill meal processing a neutral oil (asta oil) is recovered, the chemical composition of the asta oil is shown in Tables 4 and 5.

TABLE 1

Composition of products from the processing line

| | Round frozen krill | After decanter | After drier | Konstruktor Koshkin (Ukranian vessel) |
|---|---|---|---|---|
| Protein | 13.5 g/100 g | 20.9 g/100 g | 58.5 g/100 g | 60.2 g/100 g |
| Moisture | 76.3 g/100 g | 65.6 g/100 g | 9.1 g/100 g | 9.6 g/100 g |
| Lipid (Folch) | 8.6 g/100 g | 10 g/100 g | 21.8 g/100 g | 21.4 g/100 g |
| Free fatty acids | 29.8 g/100 g | 25.3 g/100 g | 24.8 g/100 g | 23.3 g/100 g |
| Total astaxanthin | 53.3 mg/kg | 81.3 mg/kg | 145 mg/kg | 126 mg/kg |

TABLE 2

Lipid class composition in products from the processing line

| Crude protein | Round frozen krill (g/100 g) | After decanter (g/100 g) | After drier (g/100 g) | Konstruktor Koshkin (Ukranian vessel) (g/100 g) |
|---|---|---|---|---|
| Wax ester/cholesterol ester | 2.5 | 3.0 | 1.9 | 3.3 |
| Triglycerides/pigments | 30.2 | 33.7 | 29.3 | 32.2 |
| Free fatty acids | 15.1 | 2.5 | 9.0 | 5.9 |
| Monoglycerides | 3.9 | Nd | 1.3 | Nd |
| PE | 6.6 | 10.4 | 7.9 | 6.3 |
| PS | 1.2 | 1.6 | 1.4 | 2.7 |
| PI | 1.9 | 2.0 | 2.1 | 3.5 |
| PC | 28 | 35.9 | 32.0 | 32.1 |
| Sphingomyeline/lyso PC | 2.0 | 0.5 | 3.0 | 3.0 |

Nd = not detected

TABLE 3

Amino acids in krill meal and stick water

| Amino acid | Total in meal (g/100 g protein) | Free in meal (g/100 g protein) | Free in stickwater (g/100 g protein) |
|---|---|---|---|
| Aspartic acid | 10.5 | 0.02 | 0.22 |
| Glutamic acid | 13.5 | 0.007 | 0.51 |

TABLE 3-continued

Amino acids in krill meal and stick water

| Amino acid | Total in meal (g/100 g protein) | Free in meal (g/100 g protein) | Free in stickwater (g/100 g protein) |
|---|---|---|---|
| Hydroxiproline | <0.5 | <0.001 | <0.05 |
| Serine | 4.2 | 0.02 | 0.13 |
| Glycine | 4.4 | 0.18 | 3.28 |
| Histidine | 2.1 | <0.01 | <0.05 |
| Arginine | 6.7 | 0.56 | 4.86 |
| Threonine | 4.1 | <0.01 | 0.22 |
| Alanine | 5.4 | 0.08 | 0.87 |
| Proline | 3.8 | 0.53 | 2.32 |
| Tyrosine | 4.0 | 0.01 | 0.2 |
| Valine | 5.0 | 0.02 | 0.13 |
| Methionine | 2.9 | <0.01 | 0.12 |
| Isoleucine | 5.0 | 0.02 | 0.1 |
| Leucine | 7.8 | 0.14 | 0.19 |
| Phenylalanine | 4.4 | 0.01 | 0.1 |
| Lysine | 7.8 | 0.02 | 0.27 |
| Cysteine/Cystine | 1.4 | <0.01 | <0.05 |
| Thryptophan | 1.1 | <0.02 | <0.05 |
| Creatinine | | <0.01 | <0.05 |
| Asparagine | | <0.01 | 0.05 |
| Glutamine | | <0.01 | <0.05 |
| 3-aminopropanoic acid | | 0.5 | 8.99 |
| Taurine | | 0.5 | 8.52 |
| 4-aminobutanoic acid | | <0.01 | <0.05 |
| Citrulline | | 0.04 | 0.14 |
| Carnosine | | <0.01 | <0.05 |
| Anserine | | <0.01 | <0.05 |
| Ornithine | | 0.02 | 1.04 |

3-aminopropanoic acid is also known as β-alanine 4-aminobutanoic acid is also known as γ-aminobutyric acid or GABA

TABLE 4

Composition and quality parameters of asta oil.

| | |
|---|---|
| Moisture | 0.14 g/100 g |
| Insoluble impurities | 0.02 g/100 g |
| Unsaponifable matter | 1.5 g/100 g |
| Nitrogen | 0.5 g/100 g |
| Free fatty acids | 0.3 g/100 g |
| Peroxide value | <2 meq peroxide/kg oil |
| Ansidine value | <1 |
| Phosphorous | 23 mg/kg |
| Phopspholipids | 575 mg/kg |
| Astaxanthin | 1245 mg/kg |

TABLE 5

Fatty acid composition of the asta oil

| Fatty Acid File | Asta oil |
|---|---|
| C4:0 | 0.00 |
| C6:0 | 0.00 |
| C8:0 | 0.00 |
| C10:0 | 0.00 |
| C12:0 | 0.00 |
| C14:0 | 17.5 |
| C14:1 | 0.00 |
| C15:0 | 0.00 |
| C16:0 | 19.3 |
| C16:1 | 9.7 |
| C18:0 | 1.2 |
| C18:1 | 22.6 |
| C18:2N6 | 1.4 |
| C18:3N6 | 0.1 |
| C18:3N3 | 0.7 |
| C18:4N3 | 3.0 |
| C20:0 | 0.1 |
| C20:1 | 1.3 |
| C20:2N6 | <0.1 |
| C20:3N6 | 0.1 |
| C20:4N6 | 0.1 |
| C20:3N3 | <0.1 |
| C20:4N3 | 0.2 |
| C20:5N3 (EPA) | 5.6 |
| C22:0 | 0.1 |
| C22:1 | 0.3 |
| C22:2N6 | 0.0 |
| C22:4N6 | <0.1 |
| C22:5N6 | 0.00 |
| C22:5N3 | 0.2 |
| C22:6N3 (DHA) | 2.00 |
| C24:1 | 0.03 |
| Total | 88.4 |
| Saturated | 38.0 |
| Monounsaturated | 33.9 |
| Polyunsaturated | 16.4 |
| Total | 88.4 |
| Omega-3 | 11.9 |
| Omega-6 | 1.6 |

Example 2

The krill meal obtained in example 1 was then ethanol extracted according to the method disclosed in JP02215351. The results showed that around 22% fat from the meal could be extracted, somewhat lower than was extracted using Folch (25%). Table 6 shows the fatty acid composition of the krill meal and the krill oil extracted from the meal using ethanol. Table 7 shows the composition and properties of the krill meal and products before and after extraction, whereas table 8 shows the lipid composition.

TABLE 6

Fatty acid distribution in krill meal (g/100 g lipid) and the ethanol extracted krill oil.

| Fatty Acid File | Krill meal | EtOH KO |
|---|---|---|
| C4:0 | 0.00 | |
| C6:0 | 0.00 | |
| C8:0 | 0.00 | |
| C10:0 | 0.00 | |
| C12:0 | 0.00 | |
| C14:0 | 7.8 | 6.4 |
| C14:1 | 0.00 | |
| C15:0 | 0.00 | |
| C16:0 | 15.8 | 14.7 |
| C16:1 | 5.1 | 4.2 |
| C18:0 | 0.9 | 0.7 |
| C18:1 | 13.4 | 11.8 |
| C18:2N6 | 1.1 | 1.2 |
| C18:3N6 | 0.1 | 0.1 |
| C18:3N3 | 0.4 | 0.4 |
| C18:4N3 | 1.1 | 0.1 |
| C20:0 | 0.1 | 0.1 |
| C20:1 | 0.8 | 0.6 |
| C20:2N6 | <0.1 | <0.1 |
| C20:3N6 | 0.1 | <0.1 |
| C20:4N6 | 0.2 | 0.2 |
| C20:3N3 | <0.1 | <0.1 |
| C20:4N3 | 0.2 | 0.2 |

TABLE 6-continued

Fatty acid distribution in krill meal (g/100 g lipid) and the ethanol extracted krill oil.

| Fatty Acid File | Krill meal | EtOH KO |
|---|---|---|
| C20:5N3 (EPA) | 10.5 | 10.4 |
| C22:0 | <0.1 | <0.1 |
| C22:1 | 0.5 | 0.4 |
| C22:2N6 | <0.1 | <0.1 |
| C22:4N6 | <0.1 | |
| C22:5N6 | 0.00 | |
| C22:5N3 | 0.2 | |
| C22:6N3 (DHA) | 5.4 | 4.8 |
| C24:1 | 0.03 | |
| Saturated | 24.6 | 21.9 |
| Monounsaturated | 19.9 | 17.0 |
| Polyunsaturated | 21.0 | 19.4 |
| | | |
| Total | 65.5 | 58.2 |
| Omega-3 | 18.2 | 17.0 |
| Omega-6 | 1.3 | |

TABLE 7

Composition and properties of the krill meal and products after extraction

| | Krill meal | Delipidated krill meal | EtOH extracted krill oil |
|---|---|---|---|
| Crude protein | 586 g/kg | 735 g/kg | |
| Fat (Folch) | 250 g/kg | 30 g/kg | |
| Moisture/ethanol | 71 g/kg | 134 g/kg | 85 g/kg |
| Astaxanthin esters | 144 mg/kg | 10 mg/kg | 117 mg/kg |
| Diesters | 110 mg/kg | 8.5 mg/kg | 117 mg/kg |
| Monoesters | 33 mg/kg | 1.8 mg/kg | 37 mg/kg |
| Biological digestable protein | 854 g/kg protein | 870 g/kg protein | |
| Flow number | 4.8 | 1.9 | |
| NH3 | 9 mg N/100 g | 0 | 3 mg N/100 g |
| TMA | 2 mg N/100 g | 0 | 70 mg N/100 g |
| TMAO | 125 mg N/100 g | 0 | 456 mg N/100 g |

TABLE 8

Lipid class distribution

| | Krill meal | Delipidated krill meal | EtOH extracted KO |
|---|---|---|---|
| Cholesterol ester | 3.5 | | |
| TG | 32.7 | 37.4 | 31.1 |
| FFA | 7.8 | 14.1 | 16.0 |
| Cholesterol | 9.1 | 8.0 | 12.6 |
| DG | 1.1 | | 3.3 |
| MG | 3.7 | | |
| Sphingolipid | | | 2.8 |
| PE | 6.5 | 2.5 | 2.7 |
| Cardiolipin | | 4.2 | |
| PI | 1.1 | 11.0 | |
| PS | 1.4 | | |
| PC | 28.6 | 20.2 | 25.3 |
| LPC | 2.9 | 2.6 | 6.2 |
| Total polar lipids | 40.6 | 40.5 | 36.9 |
| Total neutral lipids | 54.2 | 59.5 | 63.1 |

Example 3

The krill meal obtained in example 1 was then subjected to a supercritical fluid extraction method in two stages. During stage 1, 12.1% fat (neutral krill oil) was removed using neat $CO_2$ only at 300 bars, 60° C. and for 30 minutes. In stage 2, the pressure was increased to 400 bar and 20% ethanol was added (v/v) for 90 minutes. This resulted in further extraction of 9% polar fat which hereafter is called polar krill oil. The total fatty acid composition of the polar krill oil, the neutral krill oil and a commercial product obtained from Neptune Biotech (Laval, Quebec, Canada) are listed in Table 9. In addition the fatty acid composition for the phospholipids (Table 10), the neutral lipids (Table 11), the free fatty acids, diglycerides (Table 12), triglycerides, lyso-phosphatidylcholine (LPC) (Table 13), phosphatidylcholine (PC), phosphatidylethanolamine (PE) (Table 14), phosphatidylinositol (PI) and phosphatidylserine (PS) (Table 15) are shown. Table 16 shows the level of astaxanthin and cholesterol for the different fractions.

TABLE 9

Total fatty acids compositions of the krill oil products (% (w/w))

| | Total Fatty Acids | | |
|---|---|---|---|
| Fatty Acid File | Neutral KO | Polar KO | NKO |
| C4:0 | 0.00 | 0.00 | 0.00 |
| C6:0 | 0.00 | 0.00 | 0.00 |
| C8:0 | 0.00 | 0.00 | 0.00 |
| C10:0 | 0.00 | 0.00 | 0.00 |
| C12:0 | 0.47 | 0.04 | 0.24 |
| C14:0 | 22.08 | 3.28 | 12.48 |
| C14:1 | 0.33 | 0.01 | 0.17 |
| C15:0 | 0.58 | 0.36 | 0.52 |
| C16:0 | 27.03 | 29.25 | 23.25 |
| C16:1 | 0.07 | 0.01 | 8.44 |
| C18:0 | 1.72 | 1.03 | 1.42 |
| C18:1 | 30.29 | 13.57 | 18.92 |
| C18:2N6 | 2.10 | 1.96 | 1.71 |
| C18:3N6 | 0.30 | 0.21 | 0.00 |
| C18:3N3 | 0.69 | 1.02 | 1.32 |
| C18:4N3 | 0.05 | 1.81 | 3.50 |
| C20:0 | 0.06 | 0.00 | 0.05 |
| C20:1 | 1.87 | 0.80 | 1.16 |
| C20:2N6 | 0.05 | 0.05 | 0.05 |
| C20:3N6 | 0.22 | 0.73 | 0.04 |
| C20:4N6 | 0.00 | 0.00 | 0.49 |
| C20:3N3 | 0.09 | 0.09 | 0.06 |
| C20:4N3 | 0.24 | 0.51 | 0.33 |
| C20:5N3 (EPA) | 7.33 | 29.88 | 16.27 |
| C22:0 | 0.01 | 0.06 | 0.05 |
| C22:1 | 0.64 | 1.78 | 0.82 |
| C22:2N6 | 0.00 | 0.00 | 0.00 |
| C22:4N6 | 0.00 | 0.00 | 0.07 |
| C22:5N6 | 0.00 | 0.03 | 0.00 |
| C22:5N3 | 0.21 | 0.67 | 0.36 |
| C22:6N3 (DHA) | 3.51 | 12.61 | 8.17 |
| C24:0 | 0.05 | 0.00 | 0.01 |
| C24:1 | 0.03 | 0.25 | 0.11 |
| | | | |
| Total | 100.00 | 100.00 | 100.00 |
| Saturated | 52.00 | 34.01 | 38.01 |
| Monounsaturated | 33.22 | 16.43 | 29.61 |
| Polyunsaturated | 14.77 | 49.56 | 32.37 |
| | | | |
| Total | 100.00 | 100.00 | 100.00 |
| Omega-3 | 12.11 | 46.58 | 30.02 |
| Omega-6 | 2.67 | 2.98 | 2.35 |

TABLE 10

Fatty acid composition of the phospholipid fraction (% (w/w)).

| | Total Phospholipid | | |
|---|---|---|---|
| Fatty Acid File | Neutral KO | Polar KO | Neptune KO |
| C4:0 | 0.00 | 0.00 | 0.00 |
| C6:0 | 0.00 | 0.00 | 0.00 |
| C8:0 | 0.00 | 0.00 | 0.00 |
| C10:0 | 0.00 | 0.00 | 0.00 |
| C12:0 | 0.00 | 0.00 | 0.00 |
| C14:0 | 0.01 | 0.00 | 0.00 |
| C14:1 | 0.42 | 0.01 | 0.01 |
| C15:0 | 2.52 | 0.00 | 0.00 |
| C16:0 | 4.73 | 35.78 | 32.81 |
| C16:1 | 0.19 | 0.17 | 0.19 |
| C18:0 | 6.31 | 1.18 | 1.55 |
| C18:1 | 38.40 | 15.58 | 13.54 |
| C18:2N6 | 4.18 | 2.16 | 1.90 |
| C18:3N6 | 0.18 | 0.22 | 0.19 |
| C18:3N3 | 1.02 | 1.05 | 1.48 |
| C18:4N3 | 3.08 | 1.62 | 2.15 |
| C20:0 | 0.27 | 0.00 | 0.07 |
| C20:1 | 2.55 | 1.02 | 0.78 |
| C20:2N6 | 0.19 | 0.06 | 0.06 |
| C20:3N6 | 0.00 | 0.14 | 0.10 |
| C20:4N6 | 0.57 | 0.62 | 0.64 |
| C20:3N3 | 0.43 | 0.08 | 0.09 |
| C20:4N3 | 0.17 | 0.45 | 0.42 |
| C20:5N3 (EPA) | 20.58 | 25.53 | 26.47 |
| C22:0 | 0.14 | 0.06 | 0.00 |
| C22:1 | 0.00 | 2.09 | 1.94 |
| C22:2N6 | 0.25 | 0.71 | 0.85 |
| C22:4N6 | 0.44 | 0.00 | 0.03 |
| C22:5N6 | 0.11 | 0.00 | 0.00 |
| C22:5N3 | 0.00 | 0.60 | 0.63 |
| C22:6N3 (DHA) | 10.93 | 10.30 | 13.34 |
| C24:0 | 1.77 | 0.30 | 0.37 |
| C24:1 | 0.59 | 0.28 | 0.38 |
| Total | 100.00 | 100.00 | 100.00 |
| Saturated | 15.74 | 37.32 | 34.81 |
| Monounsaturated | 42.14 | 19.15 | 16.84 |
| Polyunsaturated | 42.12 | 43.53 | 48.34 |
| Total | 100.00 | 100.00 | 100.00 |
| Omega-3 | 36.22 | 39.62 | 44.56 |
| Omega-6 | 5.91 | 3.90 | 3.78 |

TABLE 11

Fatty acid composition of the total neutral lipid fraction (% (w/w)).

| | Total neutral lipid | | |
|---|---|---|---|
| Fatty Acid File | Neutral KO | Polar KO | Neptune KO |
| C4:0 | 0.00 | 0.00 | 0.00 |
| C6:0 | 0.00 | 0.00 | 0.00 |
| C8:0 | 0.00 | 0.00 | 0.00 |
| C10:0 | 0.00 | 0.00 | 0.00 |
| C12:0 | 0.00 | 0.00 | 0.00 |
| C14:0 | 20.35 | 11.31 | 18.44 |
| C14:1 | 0.30 | 0.29 | 0.25 |
| C15:0 | 0.53 | 1.53 | 0.62 |
| C16:0 | 23.79 | 0.49 | 24.11 |
| C16:1 | 12.42 | 5.22 | 11.86 |
| C18:0 | 1.54 | 3.27 | 1.67 |
| C18:1 | 26.81 | 33.09 | 23.82 |
| C18:2N6 | 1.68 | 2.37 | 1.79 |
| C18:3N6 | 0.20 | 0.23 | 0.25 |
| C18:3N3 | 0.59 | 0.62 | 0.03 |
| C18:4N3 | 0.03 | 1.27 | 0.05 |
| C20:0 | 0.07 | 0.00 | 0.06 |
| C20:1 | 1.63 | 1.41 | 1.39 |
| C20:2N6 | 0.04 | 0.00 | 0.05 |
| C20:3N6 | 0.18 | 0.94 | 0.01 |
| C20:4N6 | 0.00 | 0.00 | 0.00 |
| C20:3N3 | 0.09 | 0.00 | 0.01 |
| C20:4N3 | 0.18 | 0.41 | 0.23 |
| C20:5N3 (EPA) | 5.88 | 19.26 | 9.68 |
| C22:0 | 0.02 | 0.00 | 0.03 |
| C22:1 | 0.56 | 0.60 | 0.53 |
| C22:2N6 | 0.00 | 0.00 | 0.00 |
| C22:4N6 | 0.00 | 0.00 | 0.04 |
| C22:5N6 | 0.01 | 0.00 | 0.00 |
| C22:5N3 | 0.17 | 0.27 | 0.22 |
| C22:6N3 (DHA) | 2.74 | 17.22 | 4.64 |
| C24:0 | 0.15 | 0.00 | 0.17 |
| C24:1 | 0.03 | 0.21 | 0.06 |
| Total | 100.00 | 100.00 | 100.00 |
| Saturated | 46.45 | 16.60 | 45.10 |
| Monounsaturated | 41.75 | 40.82 | 37.91 |
| Polyunsaturated | 11.80 | 42.59 | 16.99 |
| Total | 100.00 | 100.00 | 100.00 |
| Omega-3 | 9.68 | 39.05 | 14.86 |
| Omega-6 | 2.11 | 3.54 | 2.14 |

TABLE 12

Fatty acid composition of the diglyceride and free fatty acids (% (w/w)).

| | Diglycerides | | | Free fatty acids | | |
|---|---|---|---|---|---|---|
| Fatty Acid File | Neutral KO | Polar KO | Neptune KO | Neutral KO | Polar KO | Neptune KO |
| C4:0 | 0.00 | 0.00 | 0.00 | 0.00 | 0.00 | 0.00 |
| C6:0 | 0.00 | 0.00 | 0.00 | 0.00 | 0.00 | 0.00 |
| C8:0 | 0.00 | 0.00 | 0.00 | 0.00 | 0.00 | 0.00 |
| C10:0 | 0.00 | 0.00 | 0.00 | 0.00 | 0.00 | 0.00 |
| C12:0 | 0.00 | 0.00 | 0.00 | 0.00 | 0.00 | 0.00 |
| C14:0 | 13.85 | 14.35 | 12.22 | 5.86 | 7.19 | 5.45 |
| C14:1 | 0.18 | 0.00 | 0.17 | 0.05 | 0.00 | 0.08 |
| C15:0 | 0.49 | 1.08 | 0.66 | 0.46 | 1.60 | 0.45 |
| C16:0 | 23.68 | 35.24 | 25.81 | 28.30 | 29.37 | 21.12 |
| C16:1 | 9.49 | 6.80 | 0.09 | 3.27 | 3.08 | 4.91 |
| C18:0 | 1.56 | 3.63 | 1.89 | 1.13 | 2.43 | 0.99 |
| C18:1 | 23.67 | 19.85 | 23.82 | 14.50 | 14.77 | 17.41 |
| C18:2N6 | 1.79 | 0.21 | 1.90 | 1.69 | 0.97 | 1.86 |
| C18:3N6 | 0.17 | 0.00 | 0.01 | 0.14 | 0.00 | 0.22 |
| C18:3N3 | 0.69 | 0.00 | 1.19 | 0.85 | 0.00 | 1.34 |
| C18:4N3 | 1.92 | 0.00 | 2.75 | 1.30 | 0.00 | 2.72 |
| C20:0 | 0.00 | 0.00 | 0.00 | 0.00 | 0.00 | 0.00 |
| C20:1 | 1.09 | 0.00 | 1.01 | 0.48 | 0.00 | 0.57 |
| C20:2N6 | 0.00 | 0.00 | 0.00 | 0.00 | 0.00 | 0.00 |
| C20:3N6 | 0.13 | 0.00 | 0.00 | 0.08 | 0.00 | 0.05 |
| C20:4N6 | 0.45 | 0.00 | 0.64 | 0.78 | 0.00 | 1.43 |
| C20:3N3 | 0.00 | 0.00 | 0.00 | 0.00 | 0.00 | 0.00 |
| C20:4N3 | 0.35 | 0.00 | 0.43 | 0.39 | 0.00 | 0.43 |
| C20:5N3 (EPA) | 14.03 | 9.80 | 18.00 | 24.33 | 23.57 | 25.36 |
| C22:0 | 0.18 | 0.00 | 0.10 | 0.00 | 0.00 | 0.05 |
| C22:1 | 0.41 | 0.00 | 0.57 | 0.80 | 0.69 | 0.37 |
| C22:2N6 | 0.28 | 0.00 | 0.50 | 0.46 | 0.00 | 0.54 |
| C22:4N6 | 0.00 | 0.00 | 0.00 | 0.00 | 0.00 | 0.00 |
| C22:5N6 | 0.00 | 0.00 | 0.00 | 0.00 | 0.00 | 0.00 |
| C22:5N3 | 0.20 | 0.00 | 0.27 | 0.34 | 0.00 | 0.32 |
| C22:6N3 (DHA) | 4.74 | 9.04 | 7.53 | 14.31 | 16.33 | 13.95 |
| C24:0 | 0.64 | 0.00 | 0.42 | 0.49 | 0.00 | 0.39 |
| C24:1 | 0.00 | 0.00 | 0.00 | 0.00 | 0.00 | 0.00 |
| Total | 100.00 | 100.00 | 100.00 | 100.00 | 100.00 | 100.00 |
| Saturated | 40.40 | 54.30 | 41.10 | 36.24 | 40.59 | 28.45 |

TABLE 12-continued

Fatty acid composition of the diglyceride and free fatty acids (% (w/w)).

|  | Diglycerides | | | Free fatty acids | | |
|---|---|---|---|---|---|---|
| Fatty Acid File | Neutral KO | Polar KO | Neptune KO | Neutral KO | Polar KO | Neptune KO |
| Mono-unsaturated | 34.84 | 26.64 | 25.66 | 19.09 | 18.54 | 23.34 |
| Poly-unsaturated | 24.77 | 19.06 | 33.24 | 44.67 | 40.87 | 48.22 |
| Total | 100.00 | 100.00 | 100.00 | 100.00 | 100.00 | 100.00 |
| Omega-3 | 21.95 | 18.85 | 30.18 | 41.51 | 39.90 | 44.13 |
| Omega-6 | 2.82 | 0.21 | 3.05 | 3.15 | 0.97 | 4.09 |

TABLE 13

Fatty acid composition of the triglyceride and lyso-phophatidylcholine fractions (% (w/w)).

|  | Triglycerides | | | Lyso PC | | |
|---|---|---|---|---|---|---|
| Fatty Acid File | Neutral KO | Polar KO | Neptune KO | Neutral KO | Polar KO | Neptune KO |
| C4:0 | 0.00 | 0.00 | 0.00 | 0.00 | 0.00 | 0.00 |
| C6:0 | 0.00 | 0.00 | 0.00 | 0.00 | 0.00 | 0.00 |
| C8:0 | 0.00 | 0.00 | 0.00 | 0.00 | 0.00 | 0.00 |
| C10:0 | 0.00 | 0.00 | 0.00 | 0.00 | 0.00 | 0.00 |
| C12:0 | 0.00 | 0.00 | 0.00 | 0.00 | 0.00 | 0.00 |
| C14:0 | 23.06 | 26.65 | 25.13 | 19.38 | 4.27 | 2.87 |
| C14:1 | 0.36 | 0.93 | 0.36 | 0.00 | 0.08 | 0.00 |
| C15:0 | 0.56 | 2.64 | 0.78 | 0.00 | 0.52 | 0.45 |
| C16:0 | 23.17 | 4.93 | 27.80 | 41.00 | 44.14 | 30.56 |
| C16:1 | 13.68 | 11.58 | 0.04 | 0.00 | 1.84 | 2.24 |
| C18:0 | 1.52 | 3.12 | 1.99 | 0.76 | 1.59 | 1.32 |
| C18:1 | 27.83 | 34.39 | 27.92 | 6.65 | 14.24 | 11.29 |
| C18:2N6 | 1.64 | 2.05 | 1.92 | 0.00 | 1.75 | 2.07 |
| C18:3N6 | 0.20 | 0.00 | 0.30 | 0.00 | 0.00 | 0.06 |
| C18:3N3 | 0.51 | 0.00 | 0.00 | 7.95 | 0.67 | 1.75 |
| C18:4N3 | 1.99 | 0.00 | 4.83 | 0.00 | 1.11 | 2.46 |
| C20:0 | 0.06 | 0.00 | 0.08 | 0.00 | 0.00 | 0.00 |
| C20:1 | 1.67 | 0.00 | 1.76 | 0.00 | 0.52 | 0.00 |
| C20:2N6 | 0.04 | 0.00 | 0.05 | 0.00 | 0.00 | 0.00 |
| C20:3N6 | 0.05 | 0.00 | 0.01 | 0.00 | 0.00 | 0.54 |
| C20:4N6 | 0.00 | 0.00 | 0.00 | 0.00 | 0.40 | 0.00 |
| C20:3N3 | 0.05 | 0.00 | 0.07 | 0.00 | 0.00 | 0.00 |
| C20:4N3 | 0.11 | 0.00 | 0.17 | 0.00 | 0.31 | 0.55 |
| C20:5N3 (EPA) | 2.10 | 7.97 | 4.44 | 0.00 | 18.59 | 28.48 |
| C22:0 | 0.02 | 0.00 | 0.04 | 0.00 | 0.00 | 0.00 |
| C22:1 | 0.37 | 0.00 | 0.42 | 0.00 | 1.46 | 0.91 |
| C22:2N6 | 0.00 | 0.00 | 0.00 | 0.00 | 0.00 | 0.00 |
| C22:4N6 | 0.01 | 0.00 | 0.01 | 0.00 | 0.00 | 0.00 |
| C22:5N6 | 0.00 | 0.00 | 0.01 | 0.00 | 0.00 | 0.00 |
| C22:5N3 | 0.10 | 0.00 | 0.16 | 0.00 | 0.41 | 0.62 |
| C22:6N3 (DHA) | 0.67 | 3.97 | 1.42 | 24.26 | 7.79 | 13.82 |
| C24:0 | 0.26 | 1.78 | 0.26 | 0.00 | 0.32 | 0.00 |
| C24:1 | 0.00 | 0.00 | 0.03 | 0.00 | 0.00 | 0.00 |
| Total | 100.00 | 100.00 | 100.00 | 100.00 | 100.00 | 100.00 |
| Saturated | 48.64 | 39.12 | 56.08 | 61.14 | 50.83 | 35.21 |
| Mono-unsaturated | 43.90 | 46.89 | 30.52 | 6.65 | 18.14 | 14.44 |
| Poly-unsaturated | 7.45 | 13.99 | 13.41 | 32.20 | 31.02 | 50.35 |
| Total | 100.00 | 100.00 | 100.00 | 100.00 | 100.00 | 100.00 |
| Omega-3 | 5.51 | 11.94 | 11.11 | 32.20 | 28.87 | 47.69 |
| Omega-6 | 1.94 | 2.05 | 2.30 | 0.00 | 2.15 | 2.66 |

TABLE 14

Fatty acid composition of the phosphatidylcholine and the phosphatidylserine fractions (% (w/w)).

|  | PC | | | PS | | |
|---|---|---|---|---|---|---|
| Fatty Acid File | Neutral KO | Polar KO | Neptune KO | Neutral KO | Polar KO | Neptune KO |
| C4:0 | 0.00 | 0.00 | 0.00 | 0.00 | 0.00 | 0.00 |
| C6:0 | 0.00 | 0.00 | 0.00 | 0.00 | 0.00 | 0.00 |
| C8:0 | 0.00 | 0.00 | 0.00 | 0.00 | 0.00 | 0.00 |
| C10:0 | 0.00 | 0.00 | 0.00 | 0.00 | 0.00 | 0.00 |
| C12:0 | 0.00 | 0.00 | 0.00 | 0.00 | 0.00 | 0.00 |
| C14:0 | 0.75 | 3.29 | 2.77 | 7.60 | 9.52 | 2.31 |
| C14:1 | 2.07 | 0.04 | 0.02 | 0.00 | 0.00 | 0.00 |
| C15:0 | 1.34 | 0.00 | 0.00 | 3.83 | 0.00 | 0.00 |
| C16:0 | 16.65 | 31.92 | 29.83 | 30.44 | 43.61 | 19.49 |
| C16:1 | 0.96 | 0.01 | 0.17 | 9.96 | 3.47 | 2.79 |
| C18:0 | 1.33 | 1.06 | 1.33 | 2.08 | 3.34 | 2.24 |
| C18:1 | 34.34 | 13.55 | 11.16 | 0.00 | 7.37 | 11.87 |
| C18:2N6 | 10.55 | 2.27 | 1.90 | 0.00 | 0.00 | 0.00 |
| C18:3N6 | 1.44 | 0.25 | 0.20 | 0.00 | 0.00 | 0.00 |
| C18:3N3 | 2.49 | 1.19 | 1.54 | 0.00 | 0.00 | 0.00 |
| C18:4N3 | 2.38 | 1.92 | 2.41 | 0.00 | 0.00 | 0.00 |
| C20:0 | 2.79 | 0.03 | 0.05 | 0.00 | 0.00 | 0.00 |
| C20:1 | 2.42 | 0.82 | 0.74 | 0.00 | 0.00 | 0.00 |
| C20:2N6 | 0.56 | 0.05 | 0.06 | 0.00 | 0.00 | 0.00 |
| C20:3N6 | 0.67 | 0.13 | 0.09 | 0.00 | 0.00 | 0.00 |
| C20:4N6 | 1.85 | 0.61 | 0.56 | 0.00 | 0.00 | 0.00 |
| C20:3N3 | 3.94 | 0.07 | 0.06 | 0.00 | 0.00 | 0.33 |
| C20:4N3 | 4.32 | 0.50 | 0.46 | 0.00 | 0.00 | 0.00 |
| C20:5N3 (EPA) | 1.08 | 29.85 | 30.09 | 25.84 | 15.81 | 16.35 |
| C22:0 | 0.00 | 0.05 | 0.02 | 0.00 | 0.00 | 0.00 |
| C22:1 | 2.77 | 0.00 | 1.87 | 0.00 | 0.00 | 0.00 |
| C22:2N6 | 0.00 | 0.81 | 0.97 | 0.00 | 0.00 | 0.00 |
| C22:4N6 | 0.00 | 0.01 | 0.02 | 0.00 | 0.00 | 0.00 |
| C22:5N6 | 1.49 | 0.01 | 0.00 | 0.00 | 0.00 | 0.00 |
| C22:5N3 | 1.48 | 0.67 | 0.68 | 0.00 | 0.00 | 0.00 |
| C22:6N3 (DHA) | 0.00 | 10.53 | 12.49 | 20.25 | 16.89 | 44.63 |
| C24:0 | 2.34 | 0.10 | 0.18 | 0.00 | 0.00 | 0.00 |
| C24:1 | 0.00 | 0.25 | 0.34 | 0.00 | 0.00 | 0.00 |
| Total | 100.00 | 100.00 | 100.00 | 100.00 | 100.00 | 100.00 |
| Saturated | 25.19 | 36.46 | 34.18 | 43.95 | 56.47 | 24.04 |
| Mono-unsaturated | 42.56 | 14.67 | 14.29 | 9.96 | 10.84 | 14.65 |
| Poly-unsaturated | 32.25 | 48.87 | 51.53 | 46.09 | 32.69 | 61.31 |
| Total | 100.00 | 100.00 | 100.00 | 100.00 | 100.00 | 100.00 |
| Omega-3 | 15.69 | 44.73 | 47.73 | 46.09 | 32.69 | 61.31 |
| Omega-6 | 16.56 | 4.13 | 3.81 | 0.00 | 0.00 | 0.00 |

TABLE 15

Fatty acid composition of the phosphatidylinositol and phosphatidylethanolamine fractions (% (w/w)).

|  | PI | | | PE | | |
|---|---|---|---|---|---|---|
| Fatty Acid File | Neutral KO | Polar KO | Neptune KO | Neutral KO | Polar KO | Neptune KO |
| C4:0 | 0.00 | 0.00 | 0.00 | 0.00 | 0.00 | 0.00 |
| C6:0 | 0.00 | 0.00 | 0.00 | 0.00 | 0.00 | 0.00 |
| C8:0 | 0.00 | 0.00 | 0.00 | 0.00 | 0.00 | 0.00 |
| C10:0 | 0.00 | 0.00 | 0.00 | 0.00 | 0.00 | 0.00 |
| C12:0 | 0.00 | 0.00 | 0.00 | 0.00 | 0.00 | 0.00 |
| C14:0 | 11.15 | 5.82 | 5.72 | 14.42 | 4.60 | 0.83 |
| C14:1 | 3.03 | 0.66 | 0.00 | 0.00 | 0.00 | 0.10 |
| C15:0 | 5.86 | 1.95 | 3.18 | 0.00 | 1.30 | 0.23 |
| C16:0 | 37.02 | 30.66 | 31.39 | 35.91 | 31.21 | 18.38 |
| C16:1 | 18.05 | 2.24 | 1.16 | 0.00 | 1.51 | 0.75 |
| C18:0 | 6.72 | 2.83 | 5.56 | 12.72 | 16.70 | 1.84 |
| C18:1 | 18.15 | 24.77 | 14.23 | 36.96 | 19.91 | 18.45 |

TABLE 15-continued

Fatty acid composition of the phosphatidylinositol and phosphatidylethanolamine fractions (% (w/w)).

| | PI | | | PE | | |
|---|---|---|---|---|---|---|
| Fatty Acid File | Neutral KO | Polar KO | Neptune KO | Neutral KO | Polar KO | Neptune KO |
| C18:2N6 | 0.00 | 2.67 | 0.00 | 0.00 | 2.62 | 0.85 |
| C18:3N6 | 0.00 | 0.00 | 0.00 | 0.00 | 0.00 | 0.00 |
| C18:3N3 | 0.00 | 0.00 | 0.00 | 0.00 | 0.00 | 0.33 |
| C18:4N3 | 0.00 | 0.00 | 0.00 | 0.00 | 0.00 | 0.00 |
| C20:0 | 0.00 | 0.00 | 0.00 | 0.00 | 0.00 | 0.00 |
| C20:1 | 0.00 | 0.00 | 0.00 | 0.00 | 0.00 | 0.00 |
| C20:2N6 | 0.00 | 0.00 | 0.00 | 0.00 | 0.00 | 0.00 |
| C20:3N6 | 0.00 | 0.00 | 0.00 | 0.00 | 0.00 | 1.15 |
| C20:4N6 | 0.00 | 0.00 | 0.00 | 0.00 | 0.00 | 0.00 |
| C20:3N3 | 0.00 | 0.00 | 0.00 | 0.00 | 0.00 | 0.00 |
| C20:4N3 | 0.00 | 0.00 | 0.00 | 0.00 | 0.00 | 0.00 |
| C20:5N3 (EPA) | 0.00 | 17.60 | 20.45 | 0.00 | 10.76 | 21.26 |
| C22:0 | 0.00 | 0.00 | 0.00 | 0.00 | 0.00 | 0.00 |
| C22:1 | 0.00 | 0.00 | 0.00 | 0.00 | 0.00 | 0.00 |
| C22:2N6 | 0.00 | 0.00 | 0.00 | 0.00 | 0.00 | 0.00 |
| C22:4N6 | 0.00 | 0.00 | 0.00 | 0.00 | 0.00 | 0.00 |
| C22:5N6 | 0.00 | 0.00 | 0.00 | 0.00 | 0.00 | 0.00 |
| C22:5N3 | 0.00 | 0.00 | 0.00 | 0.00 | 0.00 | 0.67 |
| C22:6N3 (DHA) | 0.00 | 10.79 | 18.32 | 0.00 | 11.39 | 35.16 |
| C24:0 | 0.00 | 0.00 | 0.00 | 0.00 | 0.00 | 0.00 |
| C24:1 | 0.00 | 0.00 | 0.00 | 0.00 | 0.00 | 0.00 |
| Total | 100.00 | 100.00 | 100.00 | 100.00 | 100.00 | 100.00 |
| Saturated | 60.76 | 41.26 | 45.84 | 63.04 | 53.81 | 21.28 |
| Mono-unsaturated | 39.24 | 27.67 | 15.39 | 36.96 | 21.42 | 19.30 |
| Poly-unsaturated | 0.00 | 31.07 | 38.77 | 0.00 | 24.77 | 59.42 |
| Total | 100.00 | 100.00 | 100.00 | 100.00 | 100.00 | 100.00 |
| Omega-3 | 0.00 | 28.40 | 38.77 | 0.00 | 22.15 | 57.43 |
| Omega-6 | 0.00 | 2.67 | 0.00 | 0.00 | 2.62 | 1.99 |

TABLE 16

Compositional data for the novel krill oil composition obtained and NKO krill oil.

| Compounds | Neptune KO | Ethanol extracted KO | Polar KO | Neutral KO |
|---|---|---|---|---|
| Astaxanthin esters | 472 mg/kg | 117 mg/kg | 580 mg/kg | 98 mg/kg |
| Astaxanthin free | 11 mg/kg | <1 mg/kg | <1 mg/kg | <1 mg/kg |
| Total cholesterol | 1 g/100 g | 12 g/100 g | <0.5 g/100 g | 5.7 g/100 g |

Example 4

Neutral lipids were extracted from krill meal (138 kg) using SFE with neat $CO_2$ (solvent ratio 25 kg/kg) at 500 bar and 75° C. The neutral lipids were fractionated at 200 bar (75° C.) and at 60 bar (35° C.) at separator S1 and S2, respectively. The extract obtained in S1 (19.6 kg) were characterized and the results can be found in Tables 17A-C. The extract in table S2 (0.4 kg) were rich in water and were not further used. Next, the polar lipids were extracted using $CO_2$ at 500 bar, 20% ethanol and at a temperature of 75° C. Using a solvent ratio of 32 (kg/kg) and collecting an extract of 18.2 kg using a separator at 60 bars and 35° C. The polar lipids were collected and analyzed (Tables 18A-C). Next, the polar lipids were mixed in a 50/50 ratio with the neutral lipids collected from S1 before finally the ethanol was removed carefully by evaporation. The product obtained was red and transparent. If the ethanol is removed before the mixing if the fractions a transparent product is not obtained. The composition of the 50/50 red and transparent product can be found in Tables 19A-C.

TABLE 17A

Fatty acid composition of the extract collected in S1

| Fatty acid | Unit | Amount |
|---|---|---|
| 14:0 | g/100 g | 18.4 |
| 16:0 | g/100 g | 22.2 |
| 18:0 | g/100 g | 1.5 |
| 16:1 n-7 | g/100 g | 10.9 |
| 18:1 (n-9) + (n-7) + (n-5) | g/100 g | 25.6 |
| 20:1 (n-9) + (n-7) | g/100 g | 1.8 |
| 22:1 (n-11) + (n-9) + (n-7) | g/100 g | 0.5 |
| 16:2 (n-4) | g/100 g | 1.3 |
| 16:4 (n-1) | g/100 g | 1.2 |
| 18:2 n-6 | g/100 g | 1.3 |
| 18:3 n-3 | g/100 g | 0.8 |
| 18:4 n-3 | g/100 g | 2.9 |
| 20:5 n-3 | g/100 g | 4.1 |
| 22:6 n-4 | g/100 g | 1.7 |

TABLE 17B

Lipid class composition of the extract collected in S1

| Lipid | Unit | Amount |
|---|---|---|
| Triacylglycerol | g/100 g | 84 |
| Diacylglycerol | g/100 g | 0.7 |
| Free fatty acids | g/100 g | 1.5 |
| Cholesterol | g/100 g | 2.7 |
| Cholesterol esters | g/100 g | 0.9 |

TABLE 17C

Miscellaneous analysis of the extract in S1.

| Compound | Unit | Amount |
|---|---|---|
| Free astaxanthin | mg/kg | 4.3 |
| Astaxanthin esters | mg/kg | 462 |
| Trimethylamin | mg N/100 g | <1 |
| Trimethylamineoxide | mg N/100 g | 2 |

TABLE 18A

Fatty acid composition of the extract collected after $CO_2$ and 20% ethanol in S1.

| Fatty acid | Unit | Amount |
|---|---|---|
| 14:0 | g/100 g | 1.3 |
| 16:0 | g/100 g | 13.8 |
| 18:0 | g/100 g | 0.6 |
| 16:1 n-7 | g/100 g | 0.9 |
| 18:1 (n-9) + (n-7) + (n-5) | g/100 g | 6.5 |
| 20:1 (n-9) + (n-7) | g/100 g | 0.6 |
| 22:1 (n-11) + (n-9) + (n-7) | g/100 g | 0.1 |
| 16:2 (n-4) | g/100 g | <0.1 |
| 16:4 (n-1) | g/100 g | <0.1 |
| 18:2 n-6 | g/100 g | 0.8 |
| 18:3 n-3 | g/100 g | 0.6 |
| 18:4 n-3 | g/100 g | 1.0 |
| 20:5 n-3 | g/100 g | 14.7 |
| 22:6 n-4 | g/100 g | 6.5 |

TABLE 18B

Lipid class composition of the extract collected after $CO_2$ and 20% ethanol in S1.

| Lipid | Unit | Amount |
| --- | --- | --- |
| Triacylglycerol | g/100 g | <0.5 |
| Cholesterol | g/100 g | <0.5 |
| Phophatidylethanolamine | g/100 g | 1.6 |
| Phosphatidylcholine | g/100 g | 67 |
| Lyso-phophatidylcholine | g/100 g | 4.4 |

TABLE 18C

Miscellaneous analysis of the extract in S1.

| Compound | Unit | Amount |
| --- | --- | --- |
| Trimethylamin | mg N/100 g | 422 |
| Trimethylamineoxide | mg N/100 g | 239 |

TABLE 19A

Fatty acid composition of the final blended product obtained in Example 4 in S1.

| Fatty acid | Unit | Amount |
| --- | --- | --- |
| 14:0 | g/100 g | 9.7 |
| 16:0 | g/100 g | 18.5 |
| 18:0 | g/100 g | 1.0 |
| 16:1 n-7 | g/100 g | 5.8 |
| 18:1 (n-9) + (n-7) + (n-5) | g/100 g | 16.0 |
| 20:1 (n-9) + (n-7) | g/100 g | 1.2 |
| 22:1 (n-11) + (n-9) + (n-7) | g/100 g | 1.0 |
| 16:2 (n-4) | g/100 g | 0.3 |
| 16:4 (n-1) | g/100 g | <0.1 |
| 18:2 n-6 | g/100 g | 1.0 |
| 18:3 n-3 | g/100 g | 0.8 |
| 18:4 n-3 | g/100 g | 2.1 |
| 20:5 n-3 | g/100 g | 10.7 |
| 22:6 n-4 | g/100 g | 4.7 |

TABLE 19B

Lipid class composition of the final blended product obtained in Example 4.

| Lipid | Unit | Amount |
| --- | --- | --- |
| Triacylglycerol | g/100 g | 53 |
| Diacylglycerol | g/100 g | 1.3 |
| Free fatty acids | g/100 g | 0.5 |
| Cholesterol | g/100 g | 0.6 |
| Cholesterol esters | g/100 g | <0.5 |
| Phophatidylethanolamine | g/100 g | <1 |
| Phosphatidylcholine | g/100 g | 42 |
| Lyso-phophatidylcholine | g/100 g | 5.9 |

TABLE 19C

Miscellaneous analysis of the final blended product obtained in example 4.

| Compound | Unit | Amount |
| --- | --- | --- |
| Free astaxanthin | mg/kg | 1.1 |
| Astaxanthin esters | mg/kg | 151 |
| Trimethylamin | mg N/100 g | 109 |
| Trimethylamineoxide | mg N/100 g | 80 |

Example 5

The asta oil obtained in example 1 was blended with the polar lipids obtained in example 4 in a ratio of 46:54 (v/v). Next the ethanol was removed by evaporation and a dark red and transparent product was obtained. The product was analyzed and the results can be found in Tables 20A-C. Furthermore, the product was encapsulated into soft gels successfully. During the encapsulation it was observed that any further increase in phospholipids and thereby viscosity will make it very difficult to encapsulate the final product.

TABLE 20A

Fatty acid composition of the final blended product obtained in Example 5.

| Fatty acid | Unit | Amount |
| --- | --- | --- |
| 14:0 | g/100 g | 8.2 |
| 16:0 | g/100 g | 17.7 |
| 18:0 | g/100 g | 1.0 |
| 16:1 n-7 | g/100 g | 4.9 |
| 18:1 (n-9) + (n-7) + (n-5) | g/100 g | 14.9 |
| 20:1 (n-9) + (n-7) | g/100 g | 1.1 |
| 22:1 (n-11) + (n-9) + (n-7) | g/100 g | 1.0 |
| 16:2 (n-4) | g/100 g | 0.4 |
| 16:4 (n-1) | g/100 g | <0.1 |
| 18:2 n-6 | g/100 g | 1.2 |
| 18:3 n-3 | g/100 g | 0.8 |
| 18:4 n-3 | g/100 g | 1.8 |
| 20:5 n-3 | g/100 g | 10.6 |
| 22:6 n-4 | g/100 g | 4.8 |

TABLE 20B

Lipid class composition of the final blended product obtained in Example 5.

| Lipid | Unit | Amount |
| --- | --- | --- |
| Triacylglycerol | g/100 g | 41 |
| Diacylglycerol | g/100 g | 0.8 |
| Free fatty acids | g/100 g | 1.2 |
| Cholesterol | g/100 g | 0.4 |
| Cholesterol esters | g/100 g | 0.3 |
| Phophatidylethanolamine | g/100 g | 0.6 |
| Phosphatidylcholine | g/100 g | 51 |
| Lyso-phophatidylcholine | g/100 g | <0.5 |
| Total polar lipids | g/100 g | 52.4 |
| Total neutral lipids | g/100 g | 43.6 |

TABLE 20C

Miscellaneous analysis of the final blended product obtained in Example 5

| Compound | Unit | Amount |
| --- | --- | --- |
| Free astaxanthin | mg/kg | 12 |
| Astaxanthin esters | mg/kg | 1302 |
| Trimethylamin | mg N/100 g | 193 |
| Trimethylamineoxide | mg N/100 g | 1.7 |

Example 6

Fresh krill was pumped from the harvesting trawl directly into an indirect steam cooker, and heated to 90 C. Water and a small amount of oil were removed in a screw press before ethoxyquin (antioxidant) was added and the denatured meal was dried under vacuum at a temperature not exceeding 80 C. After 19 months storage in room temperature, a sample of the denatured meal was extracted in two steps with supercritical $CO_2$ in laboratory scale at a flow rate of 2 ml/min at 100 C and a pressure of 7500 psi. In the second step 20% ethanol was added to the $CO_2$. The two fractions collected were combined and analyzed by HPLC using ELS detection. The phosphatidylcholine was measured to 42.22% whereas the partly decomposed phosphatidylcholine was 1.68%. This data strongly contrasts the data obtained by analysis of a krill oil sample in the marketplace that showed a content of 9.05% of phosphatidylcholine and 4.60% of partly decomposed phosphatidylcholine.

Example 7

Krill lipids were extracted from krill meal (a food grade powder) using supercritical fluid extraction with co-solvent. Initially, 300 bar pressure, 333° K and 5% ethanol (ethanol:$CO_2$, w/w) were utilized for 60 minutes in order to remove neutral lipids and astaxanthin from the krill meal. Next, the ethanol content was increased to 23% and the extraction was maintained for 3 hours and 40 minutes. The extract was then evaporated using a falling film evaporator and the resulting krill oil was finally filtered. The product obtained was then analyzed and the results can be found in Table 21.

TABLE 21

Analysis of the krill oil obtained using supercritical fluid extraction.

| Parameter | Value |
| --- | --- |
| Ethanol | 1.11% w/w |
| Water Content | 2.98% w/w |
| C20:5 n-3 (EPA) | 19.9 |
| C22:6 n-3 (DHA) | 11.3 |
| Total Omega 3 | 35.7 |
| Total Omega 6 | 3.0 |
| Total Phospholipids | 50.55 wt % |
| Ratio Omega3-PL/Total Omega 3 | 77.6% w/w |
| Ratio EPA-PL/Total EPA | 84.4% w/w |
| Ratio DHA-PL/Total DHA | 74.7% w/w |
| Triglycerides | 25.9 g/100 g |
| Astaxanthin | 2091 mg/kg |
| Peroxide Value | <0.1 |

Example 8

Krill oil was prepared according to the method described in example 7 extracting from the same krill meal. The oil was subjected to $^{31}P$ NMR analysis for the identification and quantification of the various forms of phospholipids. The analysis was performed according to the following methods: Samples (20-40 mg) were weighed into 1.5 ml centrifuge tubes. Next, NMR detergent (750 µl-10% Na cholate, 1% EDTA, pH 7.0 in $H_2O+D_2O$, 0.3 g L-1 PMG internal standard) was added. Next, the tube was placed in a oven at 60° C. and periodically shaken/sonicated until completely dispersed. The solution was then transferred to a 5 ml NMR tube for analysis. Phosphorus NMR spectra were recorded on the two-channel Bruker Avance300 with the following instrument settings: spectrometer frequency 121.498 MHz, sweep width 24,271 Hz, 64,000 data points, 30 degree excitation pulse, 576 transients were normally taken, each with an 8 second delay time and f.i.d. acquisition time of 1.35 sec. Spectra were processed with a standard exponential weighting function with 0.2 Hz line broadening before Fourier transformation.

Peaks were identified using known chemical shifts. Deacylation of samples with monomethylamine was also used on two samples for confirmation of peak identity and to achieve better peak resolution. Example spectra are presented in FIG. 1. Peak area integration gave relative molar amounts of each lipid class. Weight percent values were calculated using molecular masses calculated from a krill sample fatty acid profile (average chain length=18.6). Total PL levels were calculated from the PMG internal standard peak. The quantification of the phospholipids are shown in table 25 for both the raw material, the final product and for a commercially available krill oil (Neptune Krill Oil). The main polar ether lipids of the krill meal are alkylacylphosphatidylcholine (AAPC) at 7-9% of total polar lipids, lyso-alkylacylphosphatidylcholine (LAAPC) at 1% of total polar lipids (TPL) and alkylacylphosphatidyl-ethanolamine (AAPE) at <1% of TPL.

TABLE 22

Phospholipid profiles

| | Type B krill powder | NKO | Krill Oil obtained in Example 7 |
| --- | --- | --- | --- |
| PC | 66.0 | 68.6 | 75.3 |
| AAPC | 12.0 | 7.0 | 13.0 |
| PI | | | |
| 1LPC | 1.2 | 1.3 | 0.4 |
| PS | | | |
| 2LPC | 7.4 | 13.8 | 2.9 |
| LAAPC | 2.2 | 1.2 | 0.9 |
| PE | 6.0 | 3.4 | 3.4 |
| AAPE | | | 1.5 |
| SM | | | |
| GPC | | 1.3 | |
| DHSM | | | |
| NAPE | | 3.4 | |
| CL | 5.3 | | 2.1 |
| LPE | | | 0.5 |
| LCL | | | |
| % PL in powder or lipid sample | 8.3 | 30.0 | 47.9 |

Analysis has been carried out on the fatty acid and ether/alcohol profiles of the AAPC. The following results are presented in Table 23.

TABLE 23

Fatty acid profile of the alkylacylphosphatidylcholine.

| AAPC fatty acid composition | AAPC alcohol composition | |
| --- | --- | --- |
| | alcohol | % |
| 20:5(n-3) - 46.9%; | 16:0 | 47.6 |
| 22:6(n-3) - 36.1%; | 18:1 | 17.8 |
| 18:1(n-9) - 4.6% | 16:1 | 14.1 |
| 22:5(n-3) - 2.6% | 14:0 | 10 |
| 20:4(n-6) - 1.9% | 18:0 | 8.6 |
| 21:5(n-3) - 1.5% | 18:2 | 5.1 |
| 18:2(n-6) - 0.9% | 17:0 | 4.4 |
| 16:1(n-9) - 0.8% | 15:0-i | 2.1 |
| 16:0 - 0.7% | 15:0 | 1.7 |
| phytanic - 0.6% | 20:1 | 1.4 |
| 18:3(n-3) - 0.5% | 15:0-a | 1.3 |
| 18:4(n-3) - 0.4% | 18:0-i | 0.4 |
| 18:1(n-7) - 0.4% | | |
| 24:1 - 0.4% | | |
| 14:0 - 0.3% | | |

The rest of alcohols (i17:0, etc.), were less than 0.3% each. Only part of 20:1 was confirmed by GC-MS. Alcohol moieties composition of Krill AAPC was determined (identification was performed in the form of 1-alkyl-2,3-diTMS glycerols on GC-MS, % of total fatty alcohols were obtained by GC with FID). Ten other fatty acids were all below 0.3% by mass.

Example 9

Figure 10:
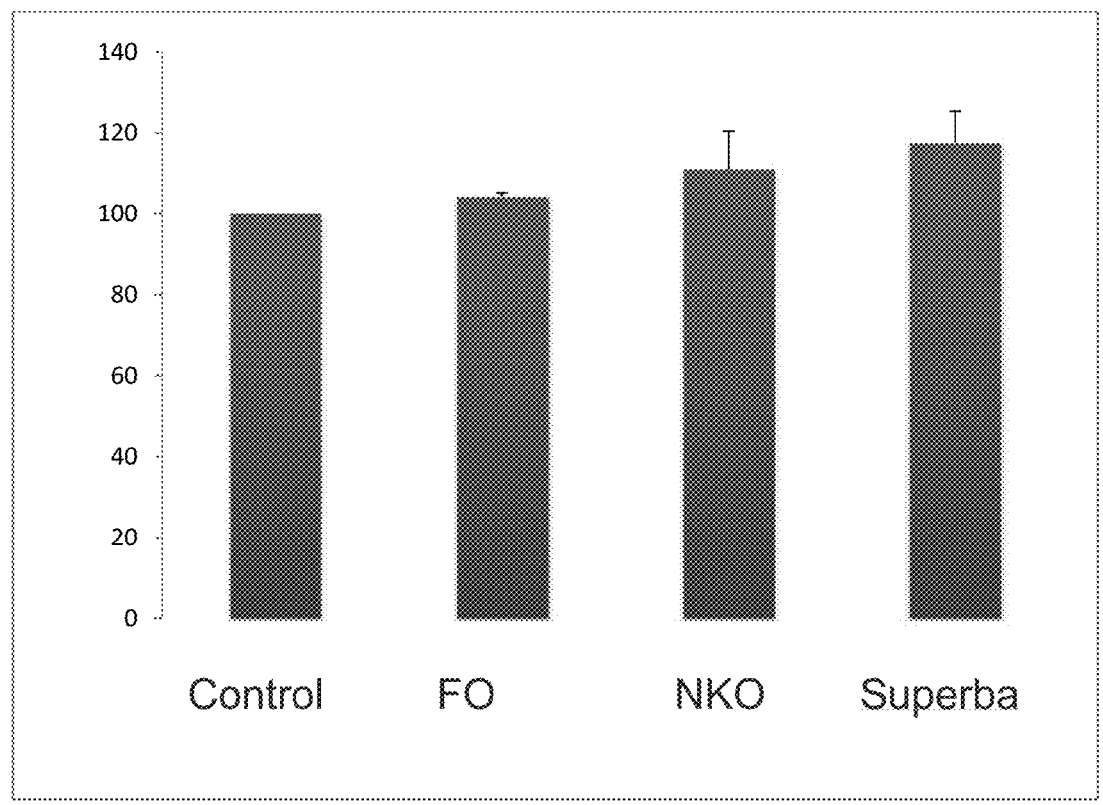
FIG. 10. Relative concentrations of DHA in the brain in Zucker rats supplemented with omega-3 fatty acids.

The purpose of this experiment was to investigate the effect of different omega-3 fatty acid sources on metabolic parameters in the Zucker rat. The Zucker rat is a widely used model of obesity and insulin resistance. Obesity is due to a mutation in the leptin receptor which impairs the regulation of intake. Omega-3 sources compared in this study were fish oil (FO) and two types of krill oil. The krill oil were either from a commercial supplier (Neptune Krill oil) or prepared according to example 7 (Superba™). Four groups of rats (n=6 per group) were fed ad lib either a control diet (CTRL) or a diet supplemented with a source of omega-3 fatty acids (FO, NKO, Superba). All diets supplied same amount of dietary fatty acids, oleic acid, linoleic acid and linolenic acid. Omega-3 diets (FO, NKO and Superba™) were additionally balanced for EPA and DHA content. The Zucker rats were 4 wk old at the start of the study with average initial weight of 250 g. At this stage the Zucker rats can be characterized as being pre-diabetic. Rats were fed the test diets for 4 wk after which they were sacrificed and blood and tissue samples were collected. Data presented in the following figures are means±SE. This example shows that supplementation of the Zucker rat with krill oil prepared as in example 7 results in an improvement of metabolic parameters characteristic of the obesity induced type two diabetic condition. The effect induced by the novel krill oil is often more pronounced than the effect of FO an in several cases greater than the effect induced by NKO. Specifically, the effects of the two types of krill oil differentiated with respect to the reduction of blood LDL cholesterol levels as well as lipid accumulation in the liver and muscle (FIG. 2-9). Furthermore, the efficacy of transfer of DHA from the diet to the brain tissue was greatest with the krill oil prepared as in example 7 (FIG. 10).

Example 11

This example describes the effect of the supplementation of human diets with krill oil, fish oil (positive control), or a negative control oil (no omega-3 fatty acids) on blood urea nitrogen (BUN).

BUN measures the amount of nitrogen in the blood that comes from urea. BUN is used as a measure of renal function. Serum creatinine is, however, considered to be a more specific measure of renal function. In this study, krill oil decreased BUN by 11.8% while creatinine levels were unchanged. Thus, it is likely that the decrease in BUN is due to some other effect than improved renal function. BUN decreases if krill oil induced diuresis i.e. excretion of urine (diuretic effect).

Figure 11:
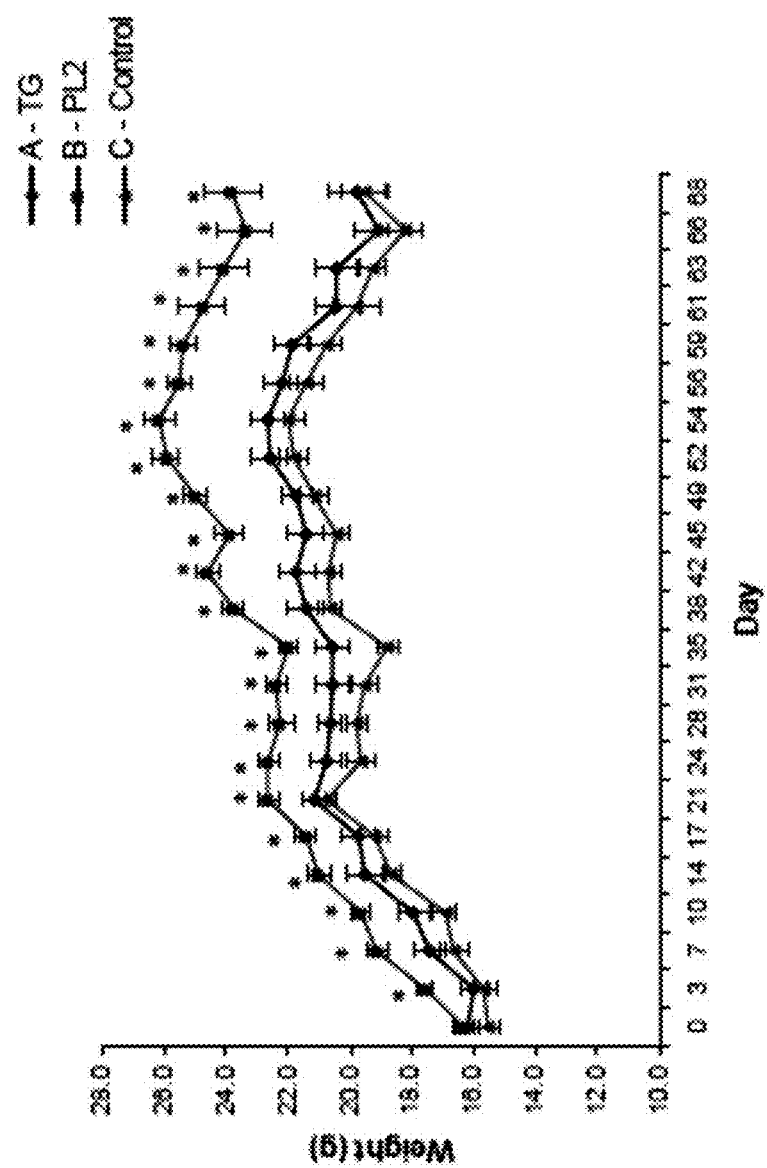
FIG. 11. Mean group body weights (g) in the collagen-induced male DBA/1 arthritic mice. B-PL2 is the krill oil group. * p<0.05, significantly different from Group A (Positive Control—Fish Oil) and Group C (Control).
Figure 12:
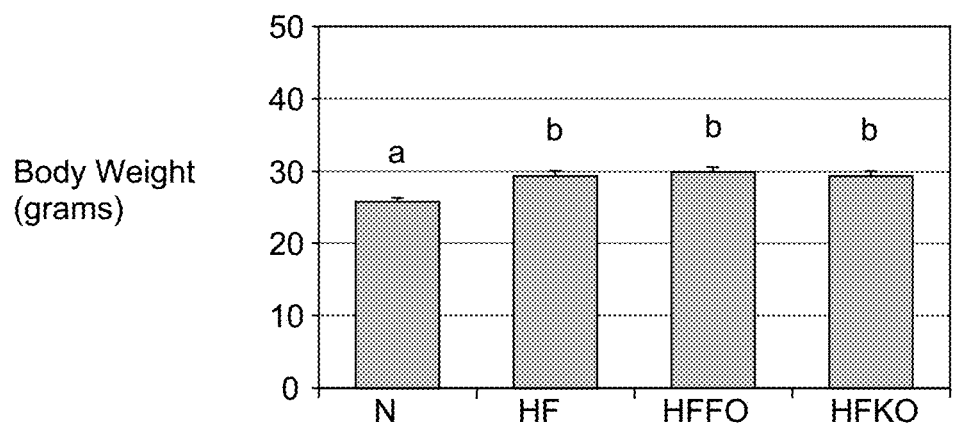
FIG. 12. Body weight for the various treatment groups.
Figure 13:
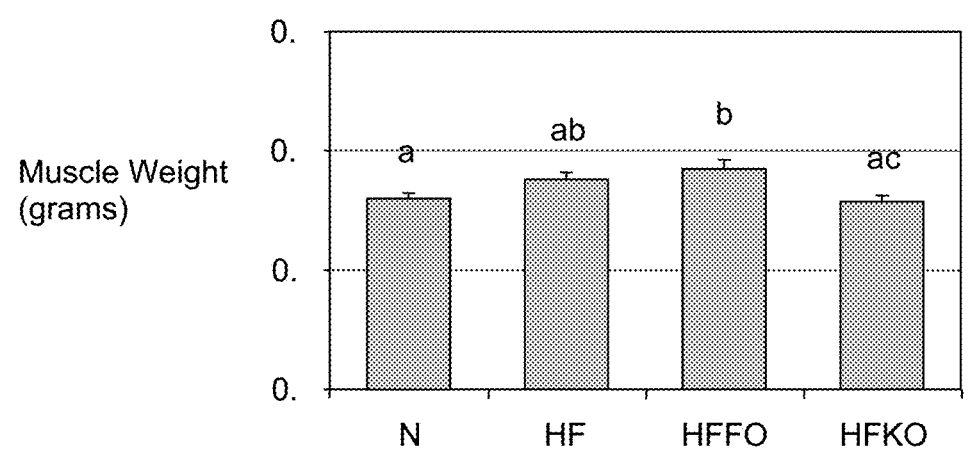
FIG. 13. Muscle weight for the various treatment groups.
Figure 14:
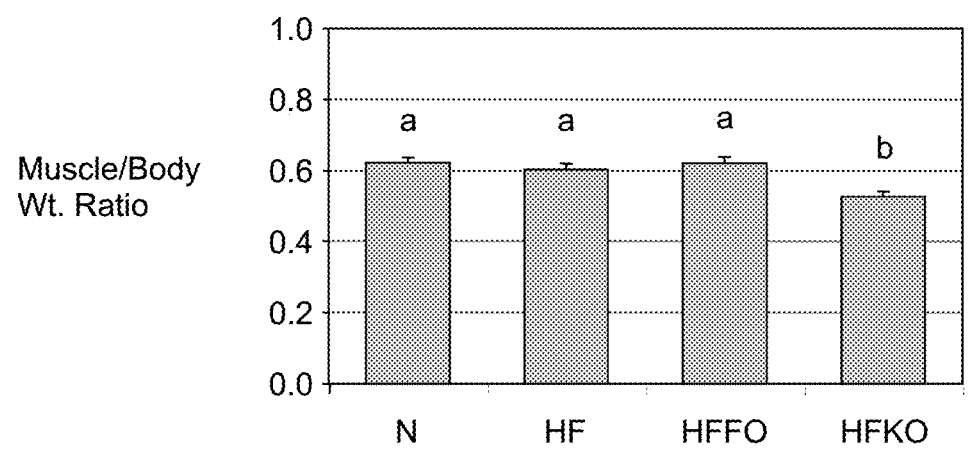
FIG. 14. Muscle to body weight ratio for the various treatment groups.
Figure 15:
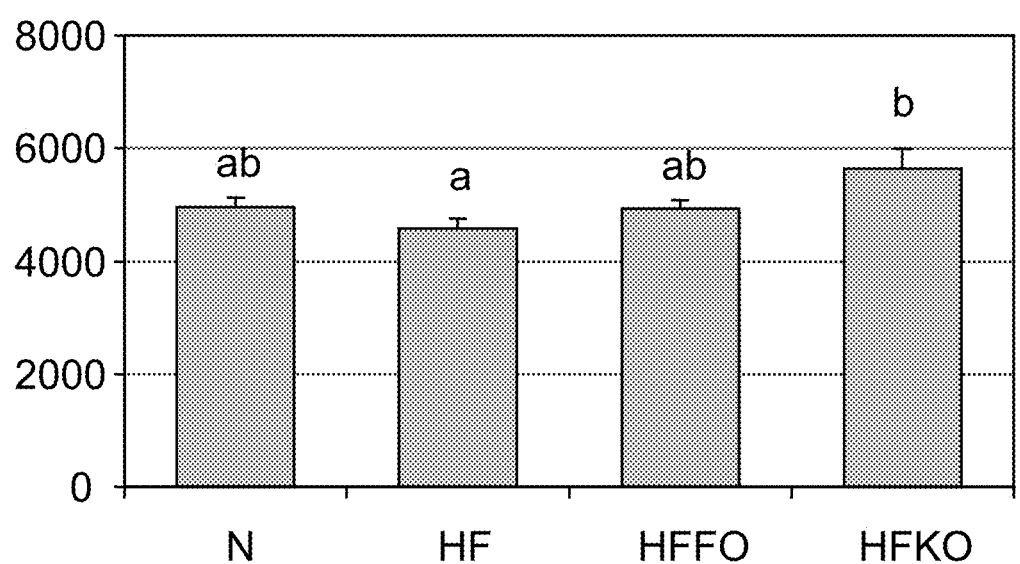
FIG. 15. Serum adiopnectin levels (ng/ml) for the various treatment groups.
Figure 16:
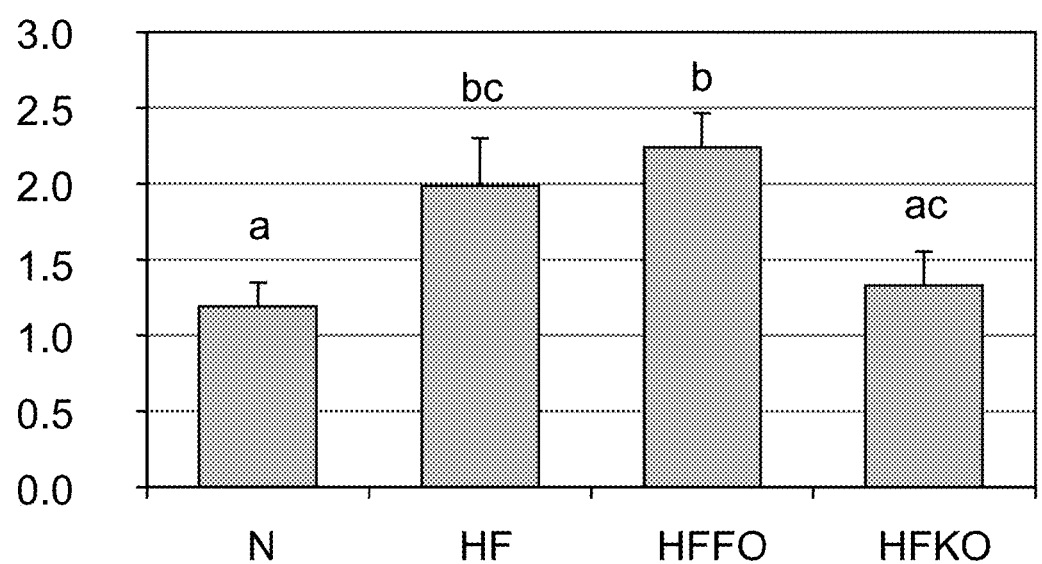
FIG. 16. Serum insulin levels for the various treatment groups.
Figure 17:
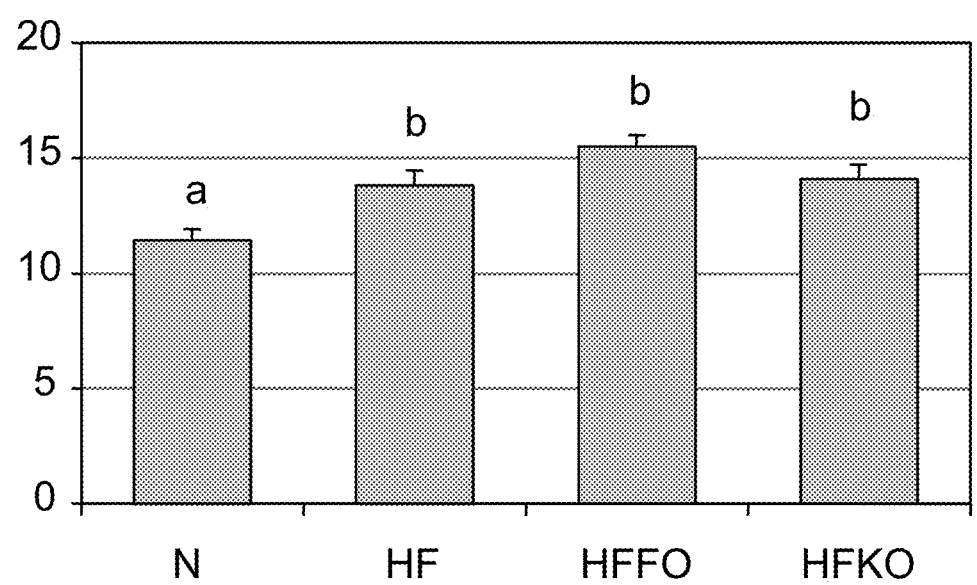
FIG. 17. Blood glucose (mmol/l) levels in the various treatment groups.
Figure 18:
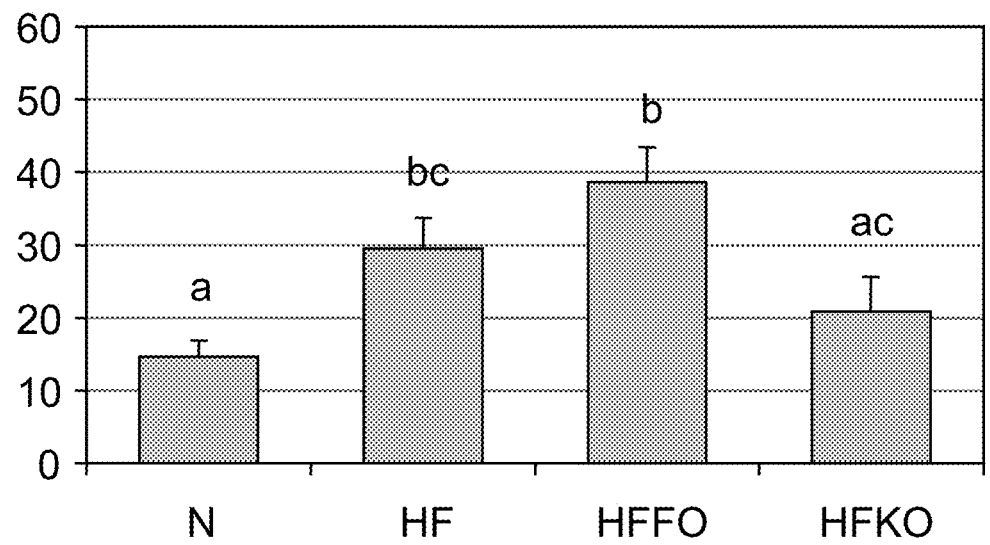
FIG. 18. HOMA-IR values for the various treatment groups.
Figure 19:
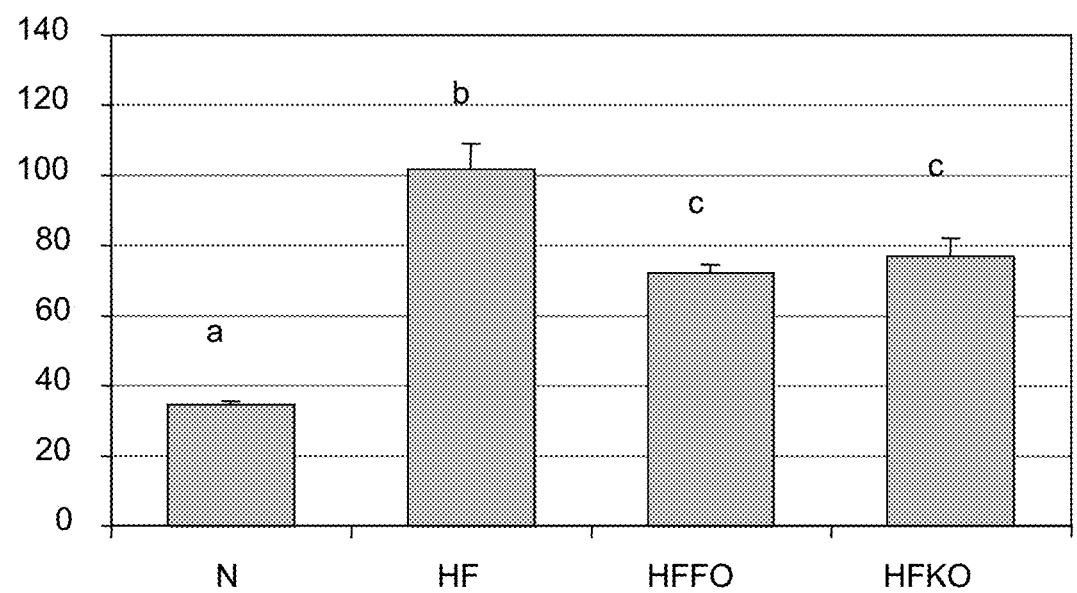
FIG. 19. Liver triglyceride levels (μmol/g) for the various treatment groups.

BUN also decreases if body protein catabolism is reduced. Protein catabolism is a normal feature of body protein turnover. Many tissues express high protein turnover rates. For example the gastrointestinal system expresses high rates of protein turnover. In growing animals a reduction in GI protein catabolism improves weight gain. Mice supplemented with krill oil grew at a faster rate than mice supplemented with fish oil or control diet (FIG. 11).

TABLE 24

The effect on blood urea nitrogen in humans for the different treatment groups.

|  | Control n = 23 | Krill Oil n = 24 | Menhaden oil n = 25 | p |
|---|---|---|---|---|
| BUN, mg/dL |  |  |  |  |
| Baseline | 11.5 (7.8, 13.8) | 11.5 (9.5, 13.5) | 11.5 (9.5, 14.0) | 0.523 |
| Δ from baseline, % | 11.0 (−14.3, 26.1) | −11.8 (−20.0, 1.5) | 9.1 (−9.1, 35.7) | 0.014r |
| Creatinine, mg/dL |  |  |  |  |
| Baseline | 0.9 (0.7, 0.9) | 0.9 (0.7, 0.9) | 0.8 (0.8, 1.0) | 0.952r (r) |
| Δ from baseline, % | 0.0 (−9.6, 2.9) | 0.0 (−2.0, 5.9) | 0.0 (−5.9, 6.7) | 0.416 |

Example 12

The purpose of this experiment was to investigate the effect of dietary krill oil on metabolic parameters in high-fat fed mice and to compare the effect of dietary krill oil with that of fish oil containing the same amount of omega-3 fatty acids. Four groups of C57BL/6 mice (n=10 per group) were fed 1) chow (N), 2) high fat diet comprising 21% butter fat and 0.15% cholesterol (HF), 3) high fat diet+krill oil (HFKO) or 4) high fat diet+fish oil (HFFO). Treatment 3 contained 2.25% (w/w) krill oil as prepared in example 5 (except that the astaxanthin content was 500 ppm) which were equivalent to 0.36% omega-3 fatty acids. Treatment 4 also contained 0.36% omega-3 fatty acids obtained from regular 18-12 fish oil. The diets were fed to the mice for 7 weeks with free access to drinking water. Data represented in this example means±SE. Columns not sharing a common letter are significantly different (P<0.05) by ANOVA followed by Tukey's multiple comparison test. N=normal chow diet (n=10); HF=high-fat diet (n=10); HFFO=high-fat diet supplemented with fish oil (n=9); HFKO=high-fat diet supplemented with krill oil (n=8). The data are presented in FIGS. 18-25.

This example shows that supplementation of high-fat fed mice with krill oil results in an amelioration of diet-induced hyperinsulinemia, insulin resistance, increase in muscle lipid content (measured as a change in muscle mass), serum adiponectin reduction and hepatic steatosis. These potentially beneficial atheroprotective effects were similar or greater than those achieved with a supplement containing a comparable level of omega-3 fatty acids (FIG. 12-19).

The invention claimed is:

1. A method of production of polar krill oil from krill comprising:

a) obtaining a krill oil;
b) extracting said krill oil with supercritical fluid extraction to provide a polar krill oil comprising greater than 4% ether phospholipids w/w of said polar krill oil; and
c) formulating said polar krill oil for oral consumption.

2. The method of claim 1, further comprising supplementing said polar krill oil with astaxanthin.

3. The method of claim 1, wherein said supercritical fluid extraction comprises use of supercritical carbon dioxide.

4. The method of claim 1, wherein said polar krill oil comprises greater than about 40% phosphatidylcholine w/w of said polar krill oil.

5. The method of claim 4, wherein said polar krill oil comprises greater than about 5% ether phospholipids w/w of said polar krill oil.

6. The method of claim 4, wherein said polar krill oil comprises greater than about 6% ether phospholipids w/w of said polar krill oil.

7. The method of claim 4, wherein said polar krill oil comprises greater than about 7% ether phospholipids w/w of said polar krill oil.

8. The method of claim 1, wherein said polar krill oil comprises greater than about 45% phosphatidylcholine w/w of said polar krill oil.

9. The method of claim 1, wherein said polar krill oil comprises less than about 25% triglycerides w/w of said polar krill oil.

10. The method of claim 1, wherein said polar krill oil comprises at least 36% omega-3 fatty acids w/w of said polar krill oil.

11. The method of claim 1, wherein said polar krill oil comprises astaxanthin.

12. The method of claim 1, wherein said formulating further comprising formulating said polar krill oil for oral consumption by a human.

13. The method of claim 8, wherein said formulating further comprises formulating said polar krill oil in a capsule.

14. The method of claim 1, wherein said krill is *Euphausia superba*.

15. A method of production of polar krill oil from *Euphausia superba* krill comprising:
a) denaturing the *Euphausia superba* krill to provide a denatured krill product;
b) extracting the denatured krill product with supercritical fluid extraction to provide a polar krill oil comprising greater than 4% ether phospholipids w/w of said polar krill oil; and
c) formulating said polar krill oil in a capsule for oral consumption by a human.

16. The method of claim 15, wherein said polar krill oil comprises greater than about 40% phosphatidylcholine w/w of said polar krill oil.

17. The method of claim 16, wherein said polar krill oil comprises greater than about 5% ether phospholipids w/w of said polar krill oil.

18. The method of claim 16, wherein said polar krill oil comprises greater than about 6% ether phospholipids w/w of said polar krill oil.

19. The method of claim 16, wherein said polar krill oil comprises greater than about 7% ether phospholipids w/w of said polar krill oil.

* * * * *